(12) United States Patent
Parra et al.

(10) Patent No.: US 10,905,617 B2
(45) Date of Patent: Feb. 2, 2021

(54) WEARABLE ASSISTIVE JAMMING APPARATUS AND RELATED METHODS

(71) Applicant: Intel Corporation, Santa Clara, CA (US)

(72) Inventors: Jeremy Parra, Beaverton, OR (US); Stephanie J. Walker, Albany, OR (US); James Hallam, Hillsboro, OR (US)

(73) Assignee: INTEL CORPORATION, Santa Clara, CA (US)

( * ) Notice: Subject to any disclaimer, the term of this patent is extended or adjusted under 35 U.S.C. 154(b) by 529 days.

(21) Appl. No.: 15/575,269

(22) PCT Filed: Dec. 19, 2016

(86) PCT No.: PCT/US2016/067510
§ 371 (c)(1),
(2) Date: Nov. 17, 2017

(87) PCT Pub. No.: WO2018/118004
PCT Pub. Date: Jun. 28, 2018

(65) Prior Publication Data
US 2018/0296424 A1    Oct. 18, 2018

(51) Int. Cl.
*A61H 3/00*    (2006.01)
*A61B 5/11*    (2006.01)
(Continued)

(52) U.S. Cl.
CPC .............. *A61H 3/00* (2013.01); *A61B 5/1114* (2013.01); *A61F 4/00* (2013.01); *A61F 5/013* (2013.01);
(Continued)

(58) Field of Classification Search
CPC ................ A61H 3/00; A61H 2003/006; A61H 2201/1238; A61H 2201/1409;
(Continued)

(56) References Cited

U.S. PATENT DOCUMENTS 5,597,189 A * 1/1997 Barbee, Sr. ............ A47G 21/08
224/218
7,056,297 B2    6/2006 Dohno et al.
(Continued)

FOREIGN PATENT DOCUMENTS

WO        2015157731        10/2015

OTHER PUBLICATIONS

International Searching Authority, "International Search Report," issued in connection with International Application No. PCT/US2016/067510, dated Sep. 13, 2017, 4 pages.
(Continued)

*Primary Examiner* — Quang D Thanh
(74) *Attorney, Agent, or Firm* — Hanley, Flight & Zimmerman, LLC

(57) ABSTRACT

Wearable assistive jamming apparatus and related methods are disclosed herein. An example apparatus includes a frame to be worn about a body part of a user and a jamming actuator carried by the frame. The example apparatus includes an electrode to deliver electricity from an electrical source communicatively coupled to the electrode to a muscle of the user. In the example apparatus, the jamming actuator is to transition from a flexible state to a substantially rigid state in coordination with the delivery of the electricity to the electrode to support the body part.

20 Claims, 6 Drawing Sheets

(51) Int. Cl.
| | |
|---|---|
| *A61N 1/36* | (2006.01) |
| *A61F 4/00* | (2006.01) |
| *G06F 3/0346* | (2013.01) |
| *A61F 5/01* | (2006.01) |
| *A61N 1/18* | (2006.01) |
| *A61N 1/02* | (2006.01) |
| *A61N 1/32* | (2006.01) |

(52) U.S. Cl.
CPC ........... *A61N 1/18* (2013.01); *A61N 1/36003* (2013.01); *A61N 1/36014* (2013.01); *A61N 1/36031* (2017.08); *A61N 1/36034* (2017.08); *G06F 3/0346* (2013.01); *A61F 2005/0155* (2013.01); *A61F 2005/0158* (2013.01); *A61F 2005/0169* (2013.01); *A61H 2003/006* (2013.01); *A61H 2201/10* (2013.01); *A61H 2201/1238* (2013.01); *A61H 2201/1409* (2013.01); *A61H 2201/5007* (2013.01); *A61H 2230/00* (2013.01); *A61N 1/025* (2013.01); *A61N 1/321* (2013.01)

(58) Field of Classification Search
CPC ........ A61H 2201/5007; A61H 2230/00; A61H 2201/10; A61F 4/00; A61F 5/013; A61F 2005/0158; A61F 2005/0169; A61F 2005/0155; G06F 3/0346; G06F 3/016; A61N 1/36034; A61N 1/18; A61N 1/321; A61N 1/025; A61N 1/36014; A61N 1/36003; A61N 1/36031; A61N 1/37252; A61N 1/0452; A61N 1/0476; A61B 5/1114; A61B 5/4836; A61B 5/6828; A61B 2562/0219; A61B 5/112; A61B 5/6825; A61B 5/6826; A63B 21/00181; A63B 23/00; A63B 24/00; A63B 2230/60; H01L 41/0986

See application file for complete search history.

(56) References Cited

U.S. PATENT DOCUMENTS

| | | | | |
|---|---|---|---|---|
| 9,266,233 | B2 | 2/2016 | Kornbluh et al. | |
| 9,314,622 | B2 | 4/2016 | Embrey et al. | |
| 9,351,900 | B2 | 5/2016 | Walsh et al. | |
| 9,403,272 | B2 | 8/2016 | Kornbluh et al. | |
| 9,427,864 | B2 | 8/2016 | Kornbluh et al. | |
| 2003/0125781 | A1 | 7/2003 | Dohno et al. | |
| 2006/0167564 | A1 | 7/2006 | Flaherty et al. | |
| 2012/0280421 | A1* | 11/2012 | Keating | A63C 19/04 264/227 |
| 2013/0275082 | A1* | 10/2013 | Follmer | G01B 21/00 702/155 |
| 2014/0128939 | A1* | 5/2014 | Embrey | A61N 1/36003 607/49 |
| 2014/0243721 | A1* | 8/2014 | Bryant | A61F 5/013 602/21 |
| 2014/0277739 | A1 | 9/2014 | Kornbluh et al. | |
| 2015/0070145 | A1 | 3/2015 | Mar et al. | |
| 2015/0148866 | A1* | 5/2015 | Bulsen | A61N 1/36014 607/48 |
| 2015/0173993 | A1 | 6/2015 | Walsh et al. | |
| 2015/0266180 | A1 | 9/2015 | Kornbluh et al. | |
| 2015/0266181 | A1 | 9/2015 | Kornbluh et al. | |
| 2015/0321339 | A1 | 11/2015 | Asbeck et al. | |
| 2016/0101516 | A1 | 4/2016 | Kornbluh et al. | |
| 2016/0101517 | A1 | 4/2016 | Kornbluh et al. | |
| 2016/0107309 | A1 | 4/2016 | Walsh et al. | |
| 2016/0220438 | A1 | 8/2016 | Walsh et al. | |
| 2016/0303369 | A1* | 10/2016 | Biasiucci | A61N 1/36003 |
| 2016/0331561 | A1 | 11/2016 | Raspopovic et al. | |
| 2016/0346156 | A1 | 12/2016 | Walsh et al. | |
| 2017/0027735 | A1 | 2/2017 | Walsh et al. | |
| 2017/0202724 | A1 | 7/2017 | De Rossi et al. | |
| 2017/0268374 | A1* | 9/2017 | Sellinger | F04D 27/0215 |

OTHER PUBLICATIONS

International Searching Authority, "Written Opinion," issued in connection with International Application No. PCT/US2016/067510, dated Sep. 13, 2017, 4 pages.

Fauconneau et al., "Continuous Wire Reinforcement for Jammed Granular," Granular Matter, May 2016, 21 pages.

Wall et al., "Selective Stiffening of Soft Actuators Based on Jamming," 2015 IEEE International Conference on Robotics and Automation (ICRA), May 26-30, 2015, pp. 252-257, 6 pages.

Polygerinos et al., "EMG Controlled Soft Robotic Glove for Assistance During Activities of Daily Living," IEEE International Conference on Rehabilitation Robotics (ICORR), Aug. 11-14, 2015, pp. 55-60, 6 pages.

Polygerinos et al., "Soft Robotic Glove for Combined Assistance and At-Home Rehabilitation," Robotics and Autonomous Systems 73, 2015, 135-143, 9 pages.

Huat, "Customizable Soft Pneumatic Gripper Devices," National University of Singapore Master Thesis, 2015, 98 pages.

Park et al., On the Feasibility of Wearable Exotendon Networks for Whole-Hand Movement Patterns in Stroke Patients, IEEE International Conference on Robotics and Automation (ICRA), May 16-21, 2016, 7 pages.

Delph II, et al., "Rehabilitative Robotic Glove," Worcester Polytechnic Institute Major Qualifying Project Report, 2012, 88 pages.

In et al., "Trend of Soft Wearable Robotic Hand," Journal of Institute of Control, Robotics and Systems, vol. 21, No. 6, 2015, 7 pages. (English abstract included).

Roam Robotics, "What Moves You," retrieved from <http://www.roamrobotics.com/our-impact/#about> on Nov. 13, 2017, 5 pages.

NASA, "Robo-Glove," retrieved from <https://technology.nasa.gov/patent/MSC-TOPS-37> on Nov. 13, 2017, 3 pages.

Rehab-Robotics, "Rehabilitation, Stroke Recovery, Neurorehabilitation, Theraputic," retrieved from <http://rehab-robotics.com> on Nov. 13, 2017, 2 pages.

In et al., "Exo-Glove: A Soft Wearable Robot for the Hand with a Soft Tendon Routing System," IEEE Robotics & Automation Magazine, vol. 22, No. 1, Mar. 12, 2015, 9 pages.

Ou et al., "jamSheets: Thin Interfaces with Tunable Stiffness Enabled by Layer Jamming," TEI '14 Proceedings of the 8th International Conference on Tangible, Embedded and Embodied Interaction, Feb. 16-19, 2014, 8 pages.

Kim et al., "A Novel Layer Jamming Mechanism with Turnable Stiffness Capability for Minimally Invasive Surgery," IEEE Transactions on Robotics, vol. 29, No. 4, Apr. 15, 2013, 12 pages.

Jiang et al., "Design of a Variable Stiffness Flexible Manipulator with Composite Granular Jamming and Membrane Coupling," IEEE International Conference on Intelligent Robots and Systems (IROS), Oct. 7-12, 2012, pp. 2922-2927, 6 pages.

Steltz et al., "Jamming as an Enabling Technology for Soft Robotics," Electroactive Polymer Actuators and Devices, Apr. 9, 2010, 9 pages.

Jiang et al., "Robotic Granular Jamming: Does the Membrane Matter?" Soft Robotics, vol. 1, No. 3, Sep. 2014, 16 pages.

Simon et al., "Wearable Jamming Mitten for Virtual Environmental Haptics," ISWC, Sep. 13-17, 2014, pp. 67-70, 4 pages.

Cheng, "Design and Analysis of Jammable Granular Systems," Massachusetts Institute of Technology, Doctoral Thesis, Jun. 2013, 110 pages.

Tome, "Exoskin—Pneumatically Augmenting Inelastic Materials for Texture Changing Interfaces," Massachusetts Institute of Technology, Master Thesis, Sep. 2015, 108 pages.

Brown et al., "Universal Robotic Gripper Based on the Jamming of Granular Material," Proceedings of the National Academy of Sciences, vol. 107, No. 44, Nov. 2, 2010, pp. 18809-18814, 6 pages.

Cheng et al., "Design and Analysis of a Robust, Low-cost, Highly Articulated Manipulator Enabled by Jamming of a Granular Media," IEEE International Conference on Robotics and Automation (ICRA), May 14-18, 2012, 6 pages.

(56) References Cited

OTHER PUBLICATIONS

Steltz et al., JSEL: Jamming Skin Enabled Locomotion, IEEE International Conference on Intelligent Robots and Systems (IROS), Oct. 11-15, 2009, pp. 5672-5677, 6 pages.

Jaeger, "Celebrating Soft Matter's 10$^{th}$ Anniversary: Toward Jamming by Design," Soft Matter, Royal Society of Chemistry, Oct. 20, 2014, 16 pages.

Bharadwaj et al., EMG Glove for Muscular Dystophy Patients, National Instruments, Jun. 23, 2010, 8 pages.

Delph II et al., "A Soft Robotic Exomusculature Glove with Integrated sEMG Sensing for Hand Rehabilitation," International Conference on Rehabilitation Robotics (ICORR), Jun. 24-26, 2013, 7 pages.

Tidwell et al., "Evaluating the Feasibility of EMG and Bend Sensors for Classifying Hand Gestures," Proceedings of the International Conference on Multimedia and Human Computer Interaction, Jul. 18-20, 2013, pp. 63-1-63-8, 8 pages.

Heo et al., "Current Hand Exoskeleton Technologies for Rehabilitation and Assistive Engineering," International Journal of Precision Engineering aand Manufacturing, vol. 13, No. 5, May 2012, pp. 807-824, 18 pages.

Tanyawiwat et al., "Design of an Assistive Communication Glove using Combined Sensory Channels," 2012 Ninth International Conference on Wearable and Implantable Body Sensor Networks, pp. 34-39, 2012, 6 pages.

Zhang et al., "Real-time Performance of Hand Motion Recognition Using Kinematic Signals for Impaired Hand Function Training," 6th Annual International IEEE EMBS Conference on Neural Engineering, pp. 339-342, Nov. 2013, 4 pages.

Yanagida et al., "Development of Endoscopic Device to Veer Out a Latex Tube with Jamming by Granular Materials," Proceeding of the IEEE International Conference on Robotics and Biomimetics (ROBIO), pp. 1474-1479, Dec. 2013, 6 pages.

Hammond III et al., "Toward a Modular Soft Sensor-Embedded Glove for Human Hand Motion and Tactile Pressure Measurement," 2014 IEEE/RSJ International Conference on Intelligent Robots and Systems (IROS 2014), pp. 4000-4007, Sep. 2014, 8 pages.

Yap et al., "A Soft Exoskeleton for Hand Assistive and Rehabilitation Application using Pneumatic Actuators with Variable Stiffness," 2015 IEEE International Conference on Robotics and Automation (ICRA), pp. 4967-4972, May 2015, 6 pages.

Jeong et al., "investigation on the Control Strategy of Soft Wearable Robotic Hand with Slack Enabling Tendon Actuator," 2015 IEEE International Conference on Robotics and Automation (ICRA), pp. 5004-5009, May 2015, 6 pages.

Popescu et al., "Development of Robotic Gloves for Hand Rehabilitation Post-Stroke," 2015 20th International Conference on Control Systems and Science, pp. 838-844, 2015, 7 pages.

Zubrycki et al., "Novel Haptic Glove-Based Interface Using Jamming Principle," Proceedings of the 10th International Workshop on Robot Motion and Control, pp. 46-51, Jul. 2015, 6 pages.

Thompson-Bean et al., "A Soft Robotic Exoskeleton Utilizing Granular Jamming," 2015 IEEE International Conference on Advanced Intelligent Mechatronics (AIM), pp. 165-170, Jul. 2015, 6 pages.

Fischer et al., "Use of a Portable Assistive Glove to Facilitate Rehabilitation in Stroke Survivors With Severe Hand Impairment," IEEE Transactions on Neural Systems and Rehabilitation Engineering, vol. 24, No. 3, pp. 344-351, Mar. 2016, 8 pages.

Biggar et al.,"Design and Evaluation of a Soft and Wearable Robotic Glove for Hand Rehabilitation," IEEE Transactions on Neural Systems and Rehabilitation Engineering, vol. 24, No. 10, pp. 1071-1080, Oct. 2016, 10 pages.

Nycz et al., "Design and Characterization of a Lightweight and Fully Portable Remote Actuation System for Use With a Hand Exoskeleton," IEEE Robotics and Automation Letters, vol. 1, No. 2, pp. 976-983, Jul. 2016, 8 pages.

Thielbar et al., "Benefits of Using a Voice and EMG-Driven Actuated Glove to Support Occupational Therapy for Stroke Survivors," IEEE Transactions on Neural Systems and Rehabilitation Engineering, vol. 25, No. 3, pp. 297-305, Mar. 2017, 9 pages.

Yap et al., "A Fabric-Regulated Soft Robotic Glove with User Intent Detection using EMG and RFID for Hand Assistive Application," IEEE International Conference on Robotics and Automation (ICRA), pp. 3537-3542, May 2016, 6 pages.

Yap et al., "A Magnetic Resonance Compatible Soft Wearable Robotic Glove for Hand Rehabilitation and Brain Imaging," IEEE Transactions on Neural Systems and Rehabilitation Engineering, vol. 25, No. 6, pp. 782-793, Jun. 2017, 12 pages.

Athanassiadis et al., "Particle Shape Effects on the Stress Response of Granular Packings," The Royal Society of Chemistry, Soft Matter, vol. 10, pp. 48-59, 2014, 12 pages.

Biroli, "A New Kind of Phase Transition?," Nature Physics, vol. 3, pp. 222-223, Apr. 2007, 2 pages.

Cheng et al., "Prosthetic Jamming Terminal Device: A Case Study of Untethered Soft Robotics," Soft Robotics, vol. 3 No. 4, pp. 205-212, 2016, 8 pages.

Trigili, "Study and Development of a Soft Semi-Active Rotational Joint for Wearable Robotics," University of Pisa, Master Thesis, available at https://etd.adm.unipi.it/t/etd-06292015-160141/, 3 pages (Abstract only).

The International Bureau, "International Preliminary Report on Patentability," issued in connection with application No. PCT/US2016/067510, dated Jun. 25, 2019, 5 pages.

\* cited by examiner

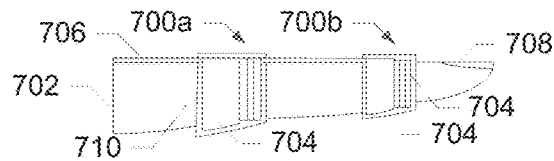 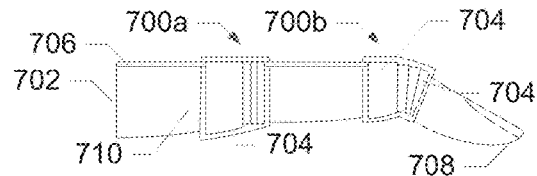
FIG. 7A                FIG. 7B
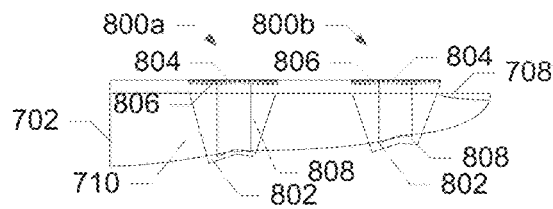 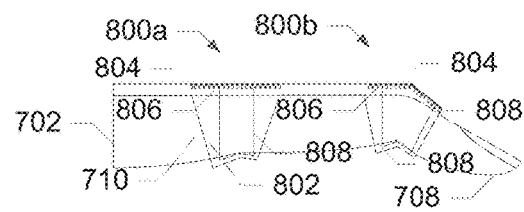
FIG. 8A                FIG. 8B
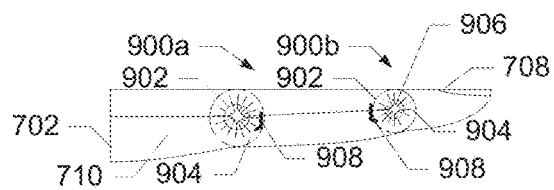 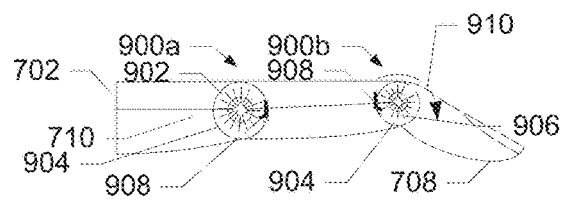
FIG. 9A                FIG. 9B
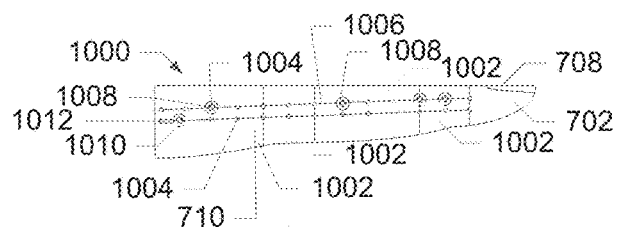 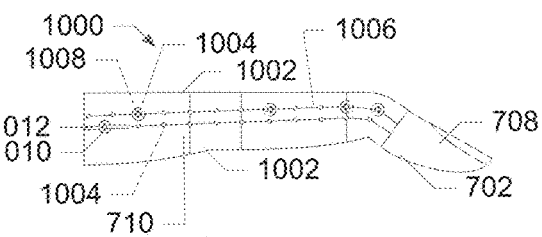
FIG. 10A               FIG. 10B
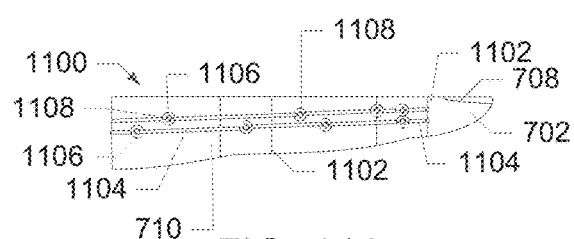 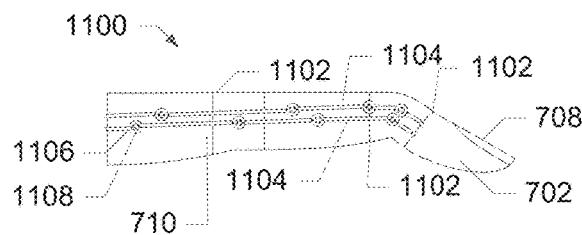
FIG. 11A               FIG. 11B

WEARABLE ASSISTIVE JAMMING APPARATUS AND RELATED METHODS

FIELD OF THE DISCLOSURE

This disclosure relates generally to wearable assistive devices and, more particularly, to wearable assistive jamming apparatus and related methods.

BACKGROUND

A wearable assistive device such as an orthotic can be used, for example, by an individual who has suffered a stroke, and who may have functional arm muscles but who has lost neurological control over those muscles after the stroke. A wearable assistive device can be used by the individual to support, for example, the person's arm and improve functioning of the person's arm muscles in performing tasks such as picking up an object. Wearable assistive technology can include therapeutic devices that electrically stimulate the muscles or an exoskeletal device that is mechanically operated via, for example, a pneumatic actuator.

BRIEF DESCRIPTION OF THE DRAWINGS

FIG. 7A is a cross-sectional view of an example jamming actuator constructed in accordance with the teachings of this disclosure and worn on a user's body part when the body part is in a first position.

FIG. 7B is a cross-sectional view of the example jamming actuator of FIG. 7A when the body part is in a second position.

FIG. 8A is a cross-sectional view of an example jamming actuator constructed in accordance with the teachings of this disclosure and worn on a user's body part when the body part is in a first position.

FIG. 8B is a cross-sectional view of the example jamming actuator of FIG. 8A when the body part is in a second position.

FIG. 9A is a cross-sectional view of an example jamming actuator constructed in accordance with the teachings of this disclosure and worn on a user's body part when the body part is in a first position.

FIG. 9B is a cross-sectional view of the example jamming actuator of FIG. 9A when the body part is in a second position.

FIG. 10A is a cross-sectional view of an example jamming actuator constructed in accordance with the teachings of this disclosure and worn on a user's body part when the body part is in a first position.

FIG. 10B is a cross-sectional view of the example jamming actuator of FIG. 10A when the body part is in a second position.

FIG. 11A is a cross-sectional view of an example jamming actuator constructed in accordance with the teachings of this disclosure and worn on a user's body part when the body part is in a first position.

FIG. 11B is a cross-sectional view of the example jamming actuator of FIG. 11A when the body part is in a second position.

Figure 1:
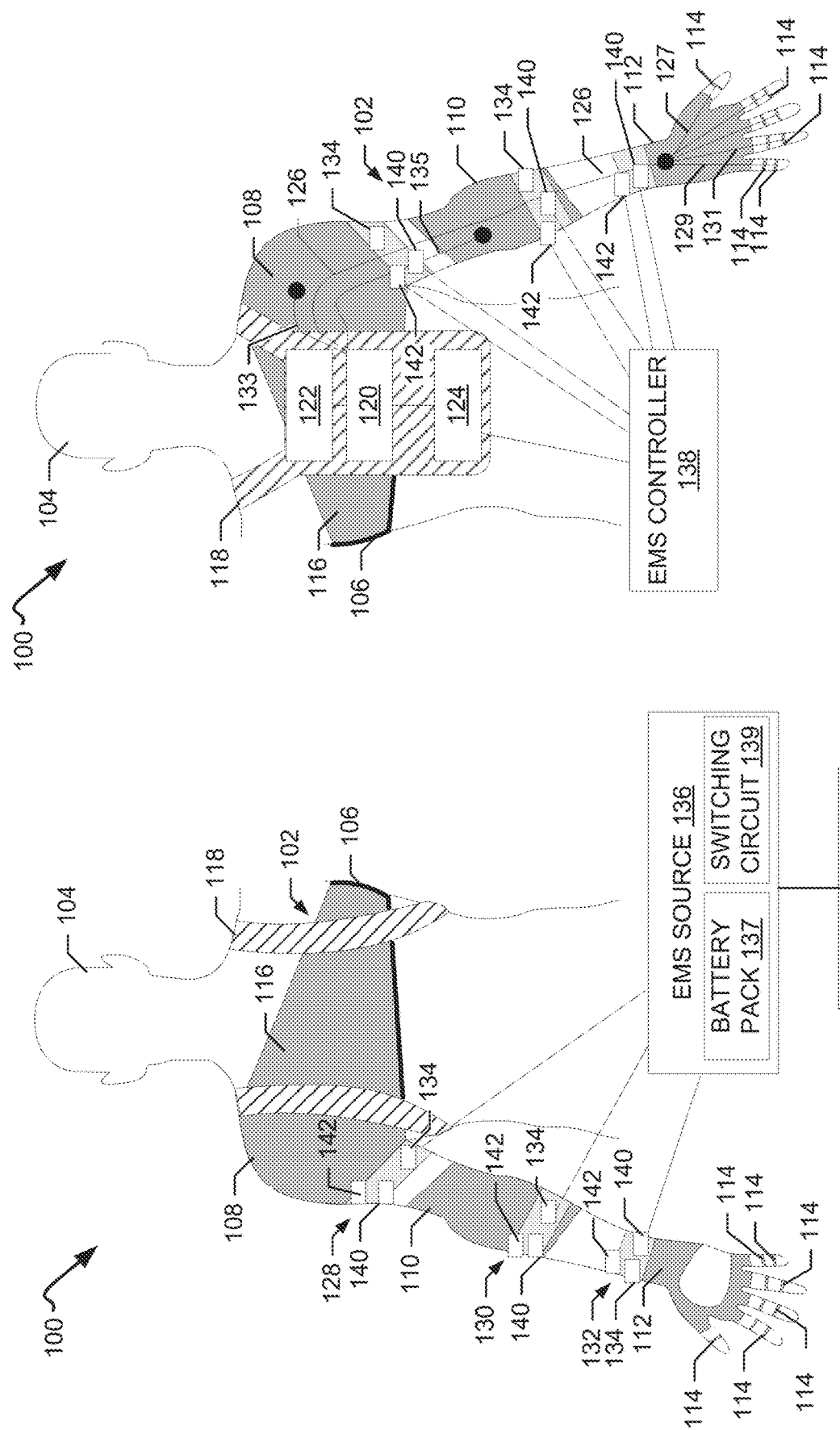
FIG. 1A is a front view of an example system constructed in accordance with the teachings disclosed herein and including a wearable assistive device and a processing unit for controlling the wearable assistive device.
FIG. 1B is a rear view of the user wearing the example wearable assistive device of FIG. 1A.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located therebetween.

DETAILED DESCRIPTION

Wearable assistive devices include orthotic devices that provide exoskeletal support for one or more limbs of a person's body to facilitate improved functioning of the limb. For example, after suffering a stroke, a person's arm muscle(s) may still be functional, but the person may lose neurological control of those muscle(s). Thus, although the arm muscle(s) may still be capable of contracting to, for example, lift the person's arm, brain signals sending instructions to the arm muscle(s) to direct the lifting may be disrupted. As a result, the person may have difficulties completing tasks such as picking up and holding an object (e.g., a cup). An orthotic device may be worn by the person on his or her arm to support and/or activate the arm muscle(s) to assist the person in using his or her arm for various tasks.

Example wearable assistive devices include devices that use one or more mechanical actuators to support, for example, an arm of a user of the device. For example, a cable-based orthotic can include a brace, such as a shoulder brace worn around a shoulder corresponding to an arm of the user for which the orthotic is to provide support. The arm can be manipulated via a series of cables that direct lifting, bending, etc. of the arm. The cables can be controlled by movement of, for example, the user's other (e.g., non-device wearing) shoulder. Although cable-based assistive devices can be effective at enabling the user to, for example, grasp an object, such devices can be uncomfortable for the user to wear and operate.

Other example orthotics use pneumatic or hydraulic actuators to generate forces that support, for example, the user's arm in a lifted position. However, assistive devices using pneumatic or hydraulic actuators have a large form factor due to the need of the actuators to expand during actuation. Thus, such assistive devices can be heavy and uncomfortable for the user to wear for extended periods of time.

Some wearable assistive technologies use electrical stimulation to cause contraction of one or more of the user's muscles. For example, a voltage from an electrical source can be applied across a muscle to cause the muscle to contract. In some examples, electromyographic (EMG) signals are measured via one or more sensors attached to the user's skin to identify activity in the user's muscles after, for example, a stroke. Electrical stimulation impulses can be applied to the muscles based on the EMG signals. Electrical stimulation applied to, for example, one of the user's fingers, can cause the user's finger to bend as a result of contraction of the finger muscles to, for example, grip an object. However, after exposure to electrical stimulation for a period time, the user's finger muscles become fatigued. As a result of fatigue, the finger muscles generate less force and may relax. When the muscles relax due to fatigue, the muscles may release from their contracted (e.g., gripping) state before the user intends the finger to release. Thus, electrical stimulation provides temporary control of a user's limbs that may be limited by muscle fatigue.

A jamming actuator is an actuator including particles such as grains (e.g., sand, diatomaceous earth, coffee grounds) disposed in an elastomeric membrane. The membrane is coupled to a vacuum pump. When the vacuum pump is activated to create a vacuum and air is removed from the membrane, the membrane stiffens due to an increase in friction between the grains and a reduction in space between the grains. Put another way, the vacuum pump causes the grains to "jam" together and the membrane to stiffen. When air is pumped into the membrane, the membrane returns to its relaxed state. A jamming actuator can be used as a gripper to pick up an object (e.g. via a robotic arm) as a result of conformance of a shape of the soft membrane about at least a portion of the object and gripping forces generated during the stiffening of the membrane.

Forces generated by granular jamming, or the application of a vacuum to grains encased in an elastomeric membrane, may be limited based on, for example, a strength of the vacuum or a thickness of the layers of the grains in the membrane. Thus, in the context of wearable assistive devices, use of granular jamming alone may be limited with respect to the ability of a jamming actuator to support a limb (e.g., a heavier limb such as an arm) and/or resist undesired muscle movements (e.g., due to fatigue). Although use of a stronger vacuum pump can result in increased gripping forces, in the context of a wearable device, use of a stronger pump can increase a weight of the wearable and/or make the wearable less portable for the user to carry.

Example systems, apparatus, and methods disclosed herein provide for a wearable assistive device that uses a combination of electrical stimulation and one or more jamming actuators to move one or more body parts of a user (such as the user's arm) to a desired limb position and/or to support the body part(s) in the limb position. The support provided by the jamming actuators when the jamming actuators are stiffened (e.g., via a vacuum force) can enable the user to perform tasks such as picking up and holding a cup. Disclosed examples utilize layered jamming techniques to provide jamming actuators that incorporate chains of grains, textured membranes, and/or components that interlock under vacuum. Disclosed jamming techniques provide improved support and increased control of motion of the user's body part(s) as compared to, for example, granular jamming alone. Disclosed jamming actuators improve the wearability of the actuators by the user to increase the user's comfort while wearing the assistive device by reducing the form factor of the device as compared to actuators including hard mechanical components (e.g., pneumatic actuators). Some examples provide jamming actuators that can be used to support smaller appendages such as the user's fingers and/or larger body parts, such as the user's arm and/or shoulder. Some examples provide a portable wearable assistive device that includes a battery powered-vacuum pump to control the actuation of the jamming actuator(s) that can be carried by the user in, for example, a back pack.

Some disclosed examples use electrical stimulation to activate the user's muscles (e.g., arm muscles) while the user is wearing the jamming enabled assistive device. In some such examples, one or more jamming actuators are disposed at the user's joints, such as the user's shoulder, elbow, wrist, and/or hand. One or more sensors such as an accelerometer can detect movement of a limb of the user, such as a voluntary positioning of the user's arm in a lifted position by the user. In response, a processor in communication with the sensors can activate electrical stimulation of the muscles of the user's arm via one or more electrodes placed on the user's skin proximate to the muscles to be activated. The electrical stimulation of the muscles can be used as a trigger for activation of a vacuum pump to actuate the jamming actuators at the respective arm joints. The stiffened jamming actuators can support the user's arm (e.g., at the shoulder, at the elbow) during electrical stimulation by transferring forces from the muscles being stimulated and/or associated joint to the jamming actuators and, thus, substantially off of the limb. This transferring can occur before and/or after the user's muscles have fatigued. In some examples, the transferring reduces (e.g., eliminates) muscle fatigue by reducing the use of electrical stimulation. In some examples, forces required to be generated by the jamming actuators to support the body parts are reduced due to the use of the user's own muscles to facilitate movement and/or to hold the limb position (e.g., via electrical stimulation or voluntary movements). In such examples, a weight of the jamming actuators and/or the vacuum pump can be reduced due to the reduced power needed by the jamming actuators to generate forces to support the limb.

Some disclosed examples combine jamming actuators with other mechanical actuators used to control the wearable. For instance, some examples include pneumatic and/or hydraulic actuators to provide for increased and/or alternative limb support. Thus, disclosed examples enhance wearable assistive devices by using jamming actuators to support the user's limb, thereby facilitating improvements in the user's ability to perform functional tasks with the limb while wearing the device.

FIGS. 1A and 1B illustrate an example system 100 constructed in accordance with the teachings of this disclosure for supporting one or more body parts of a user (e.g., a limb such as an arm of the user). The example system 100 includes a wearable assistive device (WAD) 102 to be worn by a user 104. FIG. 1A is a front view of the user 104 and the WAD 102. FIG. 1B illustrates a rear view of the user 104 wearing the WAD 102.

The example WAD 102 includes a frame 106 that is worn over own or more of the user's body parts and to which one or more components of the WAD 102 can be coupled. In the illustrated example, the frame 106 is a flexible fabric that can be worn by the user 104. In other examples, the frame 106 includes bands and/or rods to provide structural support. For example, as illustrated in FIGS. 1A and 1B, the WAD 102 can be worn such that the frame 106 extends across a chest of the user 104. The frame 106 and/or one or more portions thereof can be located at other locations along the WAD 102 (e.g., worn proximate to the user's elbow, wrist, etc.). In the example of FIGS. 1A and 1B, the WAD 102 is an arm orthotic that is worn on a shoulder, arm, wrist, and hand of the user 104 on his or her right or left side. For example purposes, FIGS. 1A and 1B illustrate the WAD 102 worn on a user's right shoulder, arm, wrist, and hand. However, the example WAD 102 can be worn on fewer body parts (e.g., just the user's forearm and hand). Also, although the WAD 102 is discussed herein in connection with the user's upper body appendages, the WAD 102 can be designed to be worn on other portions of the user's body, such as on the user's hips, legs, and/or feet. In some examples, the WAD 102 is worn on the right side, left side, or both the right and left sides of the user's body.

The example WAD 102 includes one or more jamming actuators disposed at one or more locations on the user's body where the WAD 102 is worn. The jamming actuators can be at least partially coupled to the frame 106 of the WAD 102. In the example of FIGS. 1A and 1B, the WAD 102 includes a first jamming actuator 108 proximate to the user's shoulder, a second jamming actuator 110 proximate to the user's elbow, and a third jamming actuator 112 proximate to the user's wrist. The example WAD 102 of FIGS. 1A and 1B also include a plurality of finger jamming actuators 114 disposed at the respective fingers of the user 104. As illustrated in FIGS. 1A and 1B, in some examples, two or more finger jamming actuators 114 are disposed on one or more of the user's respective fingers (e.g., at the proximal interphalangeal joint (i.e., the knuckle) and the distal interphalangeal joint (i.e., the joint closest to the fingernail))

As illustrated in the front and rear views of FIGS. 1A and 1B, the jamming actuators 108, 110, 112, 114 substantially wrap around the respective joints with which the jamming actuators are associated. In some examples, the jamming actuators 108, 110, 112, 114 also cover a portion of the body part proximate (e.g., adjacent) to the joint. For example, the second jamming actuator 110 disposed at the elbow joint can cover a portion of the user's forearm. In other examples, the jamming actuator(s) cover non-jointed portions of the user's body, such as the user's upper arm extending between the user's shoulder and elbow. The example WAD 102 of FIGS. 1A and 1B can include additional or fewer jamming actuators and/or jamming actuators worn differently than illustrated in FIGS. 1A and 1B.

The example WAD 102 of FIGS. 1A and 1B includes a vacuum source carrier 118. As shown in FIG. 1B, a vacuum pump 120, a power source 122 for the vacuum pump 120, such as a battery, and a pump controller 124 are disposed in or otherwise supported by the vacuum source carrier 118. The vacuum source carrier 118 can be, for example, a backpack that is worn by the user 104 or another type of portable carrying device (e.g., a briefcase, a rolling suitcase, a pack on a wheelchair, etc.). In other examples, the vacuum pump 120, the power source 122, and/or the pump controller 124 are not disposed in the carrier 118.

As illustrated in FIG. 1B, the example WAD 102 includes one or more vacuum pump hoses or lines 126, 127, 129, 131, 133, 135 that are coupled to the vacuum pump 120 and the respective jamming actuators 108, 110, 112, 114 (e.g., in fluid communication with the jamming actuators 108, 110, 112, 114). The respective vacuum pump hoses 126, 127, 129, 131, 133, 135 remove air from or deliver air to the jamming actuators 108, 110, 112, 114 to which the vacuum pump hoses 126, 127, 129, 131 are coupled based on whether the actuators should be actuated (e.g., stiffened) or released (e.g., softened). In some examples, the vacuum pump hoses 126, 127, 129, 131, 133, 135 include filters to prevent solid particles (e.g., grains) in the jamming actuators 108, 110, 112, 114 from traveling to the vacuum pump 120. In some examples, one of the vacuum pump hoses serves as a main line for delivering air to other vacuum pump hoses. For example, as illustrated in FIG. 1B, the vacuum pump hose 126 extends from the vacuum pump 120 to the third or wrist jamming actuator 112. Additional (e.g., capillary) vacuum pump lines 127, 129, 131 are in fluid communication with the main vacuum pump hose 126 at a junction formed at the wrist. The capillary hoses 127, 129, 131 extend from the vacuum pump hose 126 associated with the wrist jamming actuator 112 to the finger jamming actuators 114 and/or between the respective finger jamming actuators 114 worn on the user's fingers (e.g., when two finger jamming actuators 114 are worn on one finger). The pump controller 124 controls, for example, the amount of air removed from or delivered to the jamming actuator(s) 108, 110, 112, 114 via the vacuum lines 126, 127, 129, 131, 133, 135, a strength of the vacuum, etc. In some examples, the strength of the vacuum provided by the vacuum pump 120 is based on a strength required to stiffen the jamming actuator(s) 108, 110, 112, 114 to enable a jamming actuator to support a body part without compressing the body part to a degree that would cause injury.

As disclosed above, the WAD 102 includes one or more jamming actuators 108, 110, 112, 114 to support the user's body parts. The example WAD 102 of FIGS. 1A and 1B includes one or more other actuators that facilitate movement of one or more body parts of the user 104 over which the WAD 102 is worn. The one or more other actuators can include biological actuators in the form of one or more muscle(s) of the user that are electrically stimulated via a voltage applied across the muscle(s). In some examples, the one or more actuators additionally and/or alternatively include a mechanical actuator, such as a pneumatic actuator or a hydraulic actuator.

For example purposes, the WAD 102 of FIGS. 1A and 1B will be discussed in connection with the use of electrical stimulation to activate one or more of the user's muscles, which serve as biological actuators. The example WAD 102 of FIGS. 1A and 1B includes one or more openings in the WAD 102 and/or one or more positions inside the WAD 102 that provide access to the user's skin. The openings and/or interior locations 128, 130, 132 correspond to locations on the user's body where, for example, electrodes can be attached to the user's skin to electrically stimulate the muscles of the user 104 located proximate to the sites. In some examples, the openings, locations, or stimulation sites 128, 130, 132 of the WAD 102 include pockets, clips, etc. to removably secure wires associated with the electrodes to the WAD 102 (e.g., to prevent tangling or interference with the user's body). In the examples of FIGS. 1A and 1B, a first stimulation site 128 located near the user's shoulder, a second stimulation site 130 located near the user's forearm and elbow, and a third stimulation site 132 located near the user's forearm and wrist. Each of the stimulation sites 128, 130, 132 provides access to a region or a portion of the user's body for one or more electrical muscle stimulation (EMS) electrodes 134 to be attached to the skin of the user to activate one or more of the muscles proximate to the respective stimulation site. The example WAD 102 can include additional or fewer stimulation sites (e.g., via additional or fewer openings, pockets, and/or via placement of the jamming actuator(s) 108, 110, 112, 114 to selectively cover or uncover portions of the users' skin).

The EMS electrodes 134 are electrically coupled to (e.g., in circuit with) an EMS source 136 that delivers an electrical current and/or voltage to the respective EMS electrodes 134 to cause the corresponding muscle(s) to contract. For example, one or more electrical impulses can be applied across the user's bicep muscle at the EMS electrode(s) 134 of the first stimulation site 128 to cause the bicep muscle to contract. The example EMS electrodes 134 can be electrically coupled to the EMS source 136 via a wired or wireless connection, as shown in FIG. 1A. The EMS source 136 can be implemented by a battery pack 137 and a switching circuit 139. The switching circuit 139 may selectively connect one or more of the EMS electrodes 134 to the battery pack 137 to deliver current to the same. In some examples, the EMS source 136 includes circuitry for regulating the current and/or voltage output by the battery pack 137 so that a suitable level of current and/or power is delivered to the corresponding electrode when the switching circuit 139 closes the corresponding current path.

The example system 100 of FIGS. 1A and 1B includes an EMS controller 138, which may be implemented by a processor. The EMS controller 138 is communicatively coupled to the EMS source 136. The EMS controller 138 provides one or more instructions to the EMS source 136 to direct the EMS source 136 to, for example, deliver the electrical current to one or more of the EMS electrodes 134 by closing the appropriate current paths via the switching circuit 139. In the example system 100, electrical stimulation of the muscle(s) may be activated via detection of voluntary movement of one or more body parts of the user 104 (e.g., raising the arm) and/or detection of voluntary contraction of one or more of the muscles (e.g., as a result of the user 104 making a first with this hand). In some examples, actuation of one or more of the jamming actuators 108, 110, 112, 114 of the WAD 102 is triggered in response to the electrical stimulation and/or movement of the corresponding muscles.

The example WAD 102 of FIGS. 1A and 1B includes one or more body movement detection sensors 140 to detect movement(s) of the body part(s) and/or the muscle contraction(s). The body movement detection sensors 140 can include accelerometers, gyroscopes, pressure sensors, etc. In some examples, the body movement detection sensors 140 are coupled to, for examples, the frame 106 of the WAD 102, etc. The example body movement detection sensors 140 are in communication (e.g., wireless communication) with the EMS controller 138, as illustrated in FIG. 1B. The body movement detection sensors 140 can be disposed proximate to, for example, the respective first, second, and third stimulation sites 128, 130, 132 and/or other positions along the example WAD 102 proximate to, for example, the user's arm, hand, etc. to detect movement of the body part(s) in proximity to the respective sensors 140. The detected movements can be voluntary or involuntary. The detected movement can be of the assisted body part (e.g., an arm impaired by a stroke) or of a body part that does not require assistance (e.g., an arm that is unimpaired by any disability).

In the example system 100 of FIGS. 1A and 1B, when the user 104 wishes to, for example, raise his right arm (i.e., the arm on which the user 104 is wearing the example WAD 102) to, for example, reach for an object, the user 104 moves his arm into the desired position (e.g., by using his other (e.g., left) arm to raise his right arm). In other examples, one or more mechanical devices (e.g., cables, a pneumatic actuator, etc.) are used to move (e.g., raise) the user's arm.

The one or more body movement detection sensors 140 detect the movement of the user's right arm. For example, accelerometers can sense movement of the arm and/or a velocity at which the arm is moved. The body movement detection sensors 140 (e.g., the accelerometers) send signal data to the EMS controller 138, which can determine that the user 104 has moved his right arm. In other examples, the body movement detection sensors 140 include pressure sensors that send data regarding changes in pressure at, for example, the user's hand to the EMS controller 138, which can determine, for example, that the user's hand has made contact with an object (e.g., an object the user 104 intends to pick up).

Based on the data received from the body movement detection sensors 140 indicating movement of one or more body parts of the user 104 over which the WAD 102 is worn, the EMS controller 138 sends one or more instructions to the EMS source 136 to deliver electrical current and/or signal(s) to one or more of the EMS electrodes 134. In some examples, the EMS controller 138 directs the EMS source 136 to send the electrical current and/or signal(s) to the EMS electrodes 134 based on the location of the body movement detection sensor(s) 140 from which the sensor data was received. For example, if the EMS controller 138 determines that the body movement detections sensor(s) 140 proximate to the user's wrist detected motion of the wrist, the EMS controller 138 instructs the EMS source 136 to send the electrical current and/or signal(s) to the EMS electrode(s) 134 at the third stimulation site 132.

The WAD 102 of the example shown in FIGS. 1A and 1B includes one or more electromyography (EMG) sensors 142. The EMG sensors 142 can be removably attached to the user's skin at the first, second, and/or third stimulation sites 128, 130, 132 to detect electrical activity of one or more of the user's muscles (e.g., in response to the stimulation of the muscle(s) by the user's nervous system). For example, the user 104 can voluntarily contract his bicep muscle (e.g., the muscle proximate to the first stimulation site 128) or squeeze his hand to contract muscles in his fingers and hand (e.g. the muscles proximate to the third stimulation site 132). When the user's muscle(s) contract, the EMG sensor(s) 142 detect the electrical activity of the muscles and generate signals that are sent to the EMS controller 138 via a wired or wireless connection, as shown in FIG. 1B. Based on the data from the EMG sensor(s) 142, the EMS controller 138 can instruct the EMS source 136 to send electrical current and/or signal(s) to the EMS electrode(s) 134 at the stimulation site(s) 128, 130, 132 where the EMG sensor(s) 142 detected the electrical activity of the muscles to stimulate the muscles to (further) contract (e.g., to a greater degree than the user can achieve without assistance and/or for a longer period of time than the user can sustain without assistance). Thus, the EMS controller 138 determines an intent of the user 104 based on a movement and/or a position of one or more of his or her body parts (e.g., a body part over which the WAD 102 is worn) based on sensor data received from the body movement detection sensors 140 and/or the EMG sensors 142.

As an example, the user 104 may move his arm from a relaxed position (e.g., limp, substantially limp, or resting) to a raised position (e.g., lifted away from the user's side, lifted to shoulder height or above, bent at the elbow, flexed, etc.) to, for example reach for an object. Electrical stimulation via the EMS electrodes 134 can cause contraction of the upper arm muscles(s) (e.g., a bicep) of the user 104 to enable the user 104 to hold his arm in the raised position for a period of time. However, the user 104 may need additional assistance in holding up his arm as, for example, his bicep muscle(s) begin to fatigue over time. In the example of FIGS. 1A and 1B, electrical stimulation of the user's arm muscle(s) serves as a trigger for actuation of one or more of the jamming actuators 108, 110, 112, 114, which help support the user's arm in the raised position, thereby alleviating the strain on the muscle(s).

For example, as illustrated in FIG. 1B, the EMS controller 138 is communicatively coupled to the pump controller 124 (e.g., via a wired or wireless connection). As disclosed above, the EMS controller 138 generates one or more instructions to direct the EMS source 136 to provide electrical current and/or signal(s) to the EMS electrodes 134 to stimulate the user's muscles. In some examples, the EMS controller 138 also sends one or more instructions to the pump controller 124 to activate the vacuum pump 120 in coordination with delivery of the electrical current to the EMS electrodes 134 (e.g., in response to delivery of the electrical current or in preparation for the delivery of the electrical current). Activation of the vacuum pump 120 causes air to be removed from one or more of the jamming actuators 108, 110, 112, 114 via the respective vacuum pump lines 126, 127, 129, 131, 133, 135, which causes the corresponding jamming actuator(s) 108, 110, 112, 114 to stiffen. The stiffening of the jamming actuator(s) 108, 110, 112, 114 provides support to the joints and/or other body parts proximate to the respective jamming actuator(s) 108, 110, 112, 114.

For example, the first jamming actuator 108 disposed proximate to the user's shoulder and/or the second jamming actuator 110 disposed proximate to the user's elbow can be stiffened to support the user's arm in a raised position. Forces generated by the muscles to hold the arm in the raised position are transferred to, for example, the user's shoulder which is supported by the first jamming actuator 108 and/or transferred to the user's elbow, which is supported by the second jamming actuator 110. The jamming actuators 108, 110 reduce, substantially reduce, or even eliminate forces required at the shoulder and/or elbow to hold the arm in the raised position. Put another way, forces are substantially transferred off of the muscles and joints of the user's arm and onto the jamming actuators 108, 110. Thus, the stiffening of the jamming actuators 108, 110 provides rigid support for the user's arm that assists the user 104 in holding his arm in the raised position by temporarily locking the user's arm in the raised position to enable the user to maintain the position as a result of the transfer of forces to the jamming actuators.

When the user 104 wishes to release the assisted (e.g., the left or right) arm from the raised position, the user 104 can voluntarily push the assisted arm down (e.g., with an unassisted arm). In other examples, the user's right arm is moved downward via one or more mechanical devices (e.g., cables, a pneumatic actuator) and/or another limb or body part. The body movement detector sensors 140 detect a change in motion and/or position of the user's arm and send corresponding data to the EMS controller 138. In some examples, the EMG sensors 142 send data indicative of a change in electrical activity of the muscles. Based on the EMG data received from the body movement detector sensors 140 and/or the EMG sensors 142, the EMS controller 138 sends an instruction to the EMS source 136 to send an electrical current and/or signal(s) (e.g., an impulse) to the EMS electrodes 134 to cause the muscles in the user's assisted appendage to relax, the hand to open, the arm to fall, etc.

The EMS controller 138 also sends an instruction to the pump controller 124 to reverse the jamming of the jamming actuator(s) 108, 110, 112, 114. In response, the pump controller 124 directs the vacuum pump 120 to stop the removal of air from the jamming actuator(s) 108, 110, 112, 114 and/or to provide air to the jamming actuator(s) 108, 110, 112, 114 via the vacuum lines 126, 127, 129, 131, 133, 135 to cause the jamming actuator(s) 108, 110, 112, 114 to return to their flexible or soft states. As a result of the softening of the jamming actuator(s) 108, 110, 112, 114, the user's arm is no longer supported (e.g., held in place) by the jamming actuator(s) 108, 110, 112, 114 and can move to a released position.

In other examples, the activation of the vacuum pump 120 to stiffen and/or release the jamming actuator(s) 108, 110, 112, 114 is controlled by the user 104 via, for example, an on/off/reverse switch. The switch can be on a remote control and/or supported by the vacuum source carrier 118.

In other examples, the WAD 102 does not include other actuating mechanisms (e.g., electrical stimulation, mechanical actuators such as hydraulic actuators) but instead uses the jamming actuator(s) 108, 110, 112, 114 to support the user's body parts in connection with, for example, voluntary muscle contractions by the user 104. Such an example WAD 102 can be used for users who, for example, have not completely lost control of their muscles but need some assistance to perform some tasks.

Thus, the example WAD 102 of FIGS. 1A and 1B provides for selective stiffening of the jamming actuators 108, 110, 112, 114 to support the user's shoulder, arm, wrist, and/or hand (and/or other body parts over which the WAD 102 is worn). In some examples, the vacuum pump 120 causes the jamming actuator(s) 108, 110, 112, 114 to stiffen in coordination with electrical stimulation of the muscle(s) (e.g., in response to and/or in preparation for delivery of the electrical current to the muscle(s)). In some examples, data collected by the body movement detections sensor(s) 140 and/or the EMG sensors 142 triggers or drives activation of the electrical stimulation of the muscle(s) and/or the stiffening of the jamming actuator(s) 108, 110, 112, 114. The jamming actuators 108, 110, 112, 114 enable forces generated by activation of the user's muscles to be transferred to the locations where the stiffened jamming actuators 108, 110, 112, 114 support the user's body parts (e.g., elbow, knuckles). The jamming actuators 108, 110, 112, 114 hold the user's limb in a desired position to assist the user 104 in performing voluntary movements.

Figure 2:
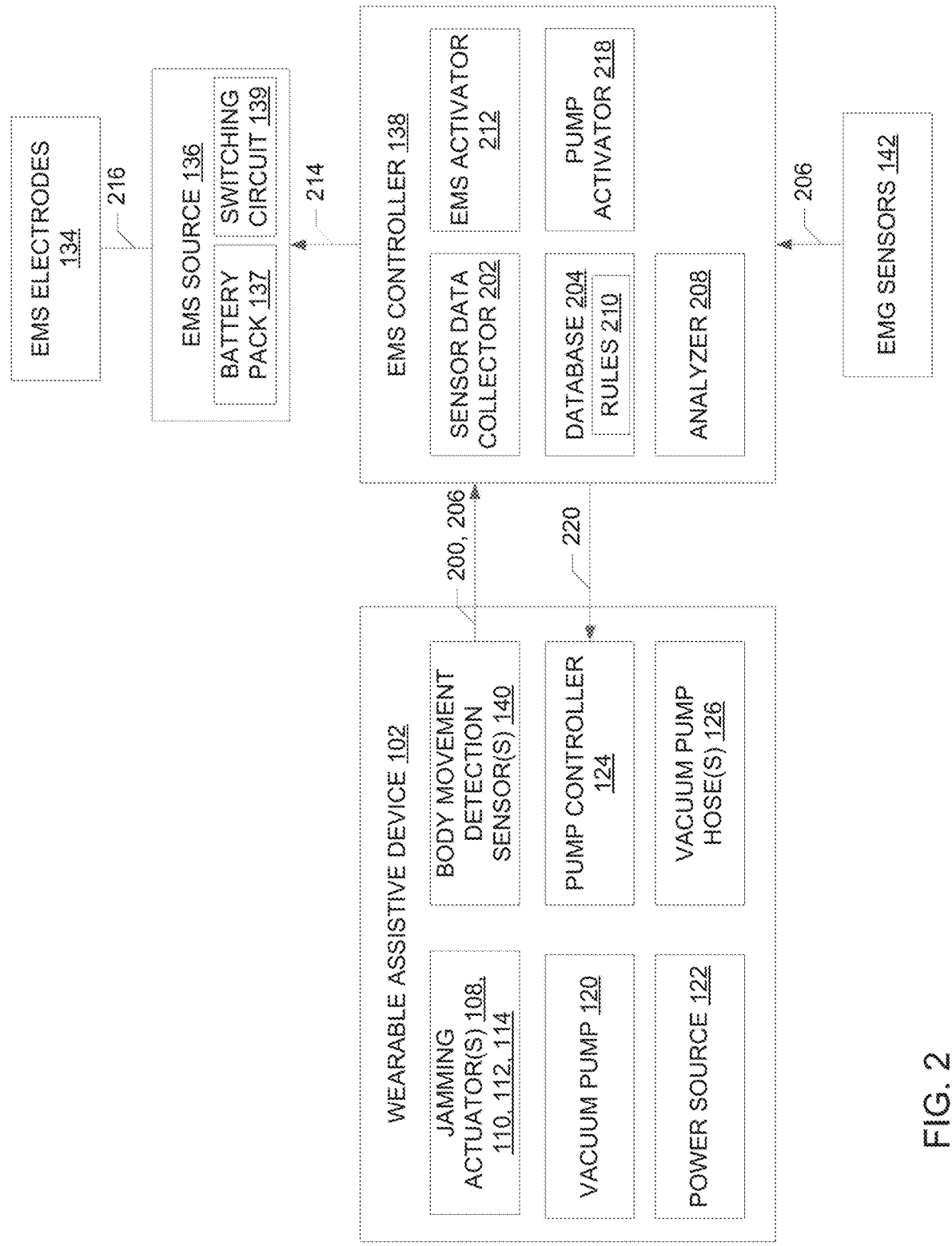
FIG. 2 is a block diagram of an example implementation of the example system of FIG. 1.

FIG. 2 is a block diagram of an example implementation of the example system 100 of FIGS. 1A and 1B. In the example of FIG. 2, the jamming actuators 108, 110, 112, 114 of the wearable assistive device (WAD) 102 can be selectively stiffened to support one or more body parts of the user 104 and/or to enable the user 104 to perform one or tasks such as grasping and lifting an object.

As disclosed above in connection with FIGS. 1A and 1B, the user 104 wears the WAD 102 over one or more parts of his or her body. For example, the user 104 can wear the WAD 102 over his or her shoulder, arm, wrist, and/or hand on the right or left side of his or her body while performing tasks such as reaching for and picking up objects such as a pencil, a fork, a cup, etc. In other examples, the user 104 wears the WAD 102 over other body parts, such as his or her leg and/or foot. In some examples, the user 104 wears the WAD 102 over one or more body parts on the right, left, or both right and left sides of his or her body.

An example implementation of a WAD 102 is shown in FIG. 2. Other WADs 102 can include similar or different components, depending on the application, the body location on which the WAD is worn, etc. The example WAD 102 includes the jamming actuators 108, 110, 112, 114. The jamming actuators 108, 110, 112, 114 can be disposed relative to the user's joints, such as at, adjacent, and/or over his or her shoulder joint, elbow joint, wrist joint, and finger joint(s), as illustrated in FIGS. 1A and 1B. In other examples, the jamming actuators 108, 110, 112, 114 are located relative to different joints (e.g., the knee joint) and/or non-jointed portions of the user's body (e.g., the forearm). In other examples, the WAD 102 includes additional or fewer jamming actuators disposed relative to one or more of the same or different body parts than shown in the figures and/or disclosed here.

The example WAD 102 of FIG. 2 includes the vacuum pump 120. The vacuum pump 120 is powered by the power source 122 (e.g., a battery). In some examples, the power source 122 is implemented by the battery pack 137 of the EMS source 136. When activated, the vacuum pump 120 removes air from the jamming actuator(s) 108, 110, 112, 114 to stiffen the jamming actuators 108, 110, 112, 114 or provides air to the jamming actuator(s) 108, 110, 112, 114 to soften the actuators via the vacuum pump hose(s) 126, 127, 129, 131, 133, 135 coupled to the vacuum pump 120 and the jamming actuator(s). The example WAD 102 includes a pump controller 124 (e.g., a processor) to control, for example, the vacuum forces generated by the vacuum pump 120.

One or more body movement detection sensors 140 are carried by the WAD 102 (e.g., coupled to the frame 106 of the WAD 102). The body movement detection sensors 140 can include accelerometers, pressure sensors, and/or other types of sensors capable of detecting movement, position, acceleration, velocity, blood pressure, temperature, etc. of the one or more of the user's body parts over which the WAD 102 is worn. For example, an accelerometer can detect that a user's arm has moved. Tracking blood pressure and/or temperature may be useful to ensure an appendage is not being held in a position too long or otherwise being manipulated so as to cause injury.

In the example of FIG. 2, the body movement detection sensors 140 send data 200 about the body movement, pressure activity (e.g., pressure exerted as a result making contact with an object), etc. to the electrical muscle stimulation (EMS) controller 138. The body movement detection sensors 140 send the signal data 200 to the EMS controller 138 in substantially real-time as the user 104 moves one or more of his body parts to a desired position (e.g., via voluntary movements, with the assistance of a mechanical, electrical, and/or pneumatic device, etc.).

The EMS controller 138 of FIG. 2 can be, for example, a processor of a computing device disposed proximate to the user 104 while the user 104 is wearing the WAD 102 (e.g., a computer in the same room as the user 104). In other examples, the EMS controller 138, the EMS source 136, and the EMS electrodes 134 are carried by the WAD 102. The example EMS controller 138 includes a sensor data collector 202. The sensor data collector 202 receives the data 200 generated by the body movement detection sensors 140. The sensor data collector 202 processes the raw signals 200 collected by the body movement detection sensors 140 to, for example, amplify the signal(s) 200, filter the signal(s) 200, remove noise from the signal(s) 200, and/or decode the signal(s) into data 200 (e.g. via an analog to digital converter). The data 200 is stored in a database 204 of the EMS controller 138. In some examples, the database 204 stores information about the location of the body movement detection sensor(s) 140 relative to the user's body parts and the WAD 102 (e.g., at the wrist, the shoulder, etc.).

In the example of FIG. 2, the sensor data collector 202 also receives EMG data 206 from EMG sensors 142. The EMG sensors 142 can be coupled to the skin of the user 104 wearing the WAD 102. For example, the EMG sensors 142 can be coupled to the user's skin at stimulation sites (e.g., one or more positions inside the WAD 102 and/or one or more openings in the WAD 102 that provide access to the user's skin such as the stimulation sites 128, 130, 132 of FIGS. 1A and 1B). In some examples, the database 204 stores information about the location of the EMG sensors 142 relative to the user's body parts and the WAD 102 (e.g., at the bicep, the deltoid, etc.).

The EMG sensors 142 detect electrical activity of the user's muscles (either in response to voluntary contractions or involuntary (e.g., assisted) contractions of the user's muscles) and generate the EMG signal(s) 206. The EMG sensors 142 send the EMG signal(s) 206 to the EMS controller 138 in substantially real-time. The example sensor data collector 202 processes the raw EMG signal(s) 206 (e.g., amplifies, filters, removes noise, decodes and/or coverts from analog to digital) to obtain the EMG data 206 carried by the EMG signals 206. The EMG data 206 is stored in the database 204 of the EMS controller 138.

The example EMS controller 138 of FIG. 2 includes an analyzer 208. The analyzer 208 analyzes the data 200 received from the body movement detection sensor(s) 140 and/or the EMG data 206 received from the EMG sensors 142. The analyzer 208 of FIG. 2 determines an intention of the user 104 with respect to a desired limb position (e.g., lifted, bent, gripping, etc.) of one or more body parts based on the data 200, 206 received from the body movement detection sensor(s) 140 and/or the EMG sensors 142. In some examples, the analyzer 208 applies one or more rules 210 to determine the user's intent. The rules 210 can include predefined thresholds of movement and/or EMG activity for determining that the user 104 intends to move, for example, his arm. Different rules/thresholds may apply to different body parts. The rules 210 can be input by, for example, a user of the EMS controller 138 (e.g., a healthcare professional) and stored in the database 204.

For example, the analyzer 208 can analyze position data in the data 200 received from the body movement detection sensor(s) 140 indicating that there has been a change in a position of the user's arm (e.g., relative to previously collected data 200). If the data 200 indicating a change in position exceeds a predefined threshold in the correct polarity (e.g., upward motion as opposed to downward motion), the analyzer 208 determines that the user 104 intends to lift his or her arm. If the data 200 indicating a change in position does not exceed the predefined threshold, then the analyzer 208 determines that the detected movement is an anomaly, such as a movement by the user to readjust his arm for comfort purposes or an involuntary movement (e.g., a reflex, a spasm) rather than an intentional movement. In some examples, the analyzer 208 determines which body part(s) the user 104 moved based on a location of the sensors 140 from which the data 200 is obtained and sensor location information stored in the database 204.

The analyzer 208 can apply one or more rules 210 to the EMG data 206. For example, the analyzer 208 can analyze the EMG data 206 to determine if the electrical activity (e.g., EMG signals) generated by the user's finger muscles meets predefined thresholds (e.g., a threshold amplitude) to indicate contraction of the user's fingers muscles. In some examples, the rules 210 are specific to the user 104 and/or are based on the user's condition (e.g., stroke recovery) such that the rules 210 are tailored (e.g., customized) based on the user's muscular strength and/or neurological abilities. Such rule customization can improve an accuracy of the analyzer 208 in recognizing intended movements by the user (e.g., so that even small electrical activity is recognized as an intended muscle contraction for a user who has significantly lost muscle control). In some such examples, the small electrical activity may need to be sustained for at least a threshold period of time in order to distinguish it from involuntary spasms or the like. In some examples, the analyzer 208 determines which muscles are generating the electrical (e.g., EMG) activity based on a location of the EMG sensors 142 from which the EMG data 206 is obtained and sensor location information stored in the database 204.

If the analyzer 208 determines that the user 104 intends to move one or more body parts (e.g., to assume a selected limb position), the analyzer 208 communicates with an EMS activator 212 of the EMS controller 138 of FIG. 2. The analyzer 208 sends a message to the EMS activator 212 that the user 104 has made a voluntary movement of one or more of his body parts. Based on the data received from the analyzer 208, the EMS activator 212 generates one or more EMS instructions 214 directing the EMS source 136 to provide electrical current to or respective one(s) of the EMS electrodes 134 to stimulate the muscles corresponding to the one or more body parts that the user 104 intends to use, as determined by the analyzer 208. Based on the EMS instructions 214 received from the EMS activator 212 (e.g., via a wired or wireless connection), the EMS source 136 causes the switching circuit 139 to make appropriate connections (e.g., by changing one or more switch states (e.g., from open to closed)) to thereby generate an electrical current 216 to be delivered to the correct EMS electrodes 134 to stimulate the muscles proximate to the locations on the user's skin to which the EMS electrodes 134 are coupled.

The stimulation of the user's muscles via the electrical current 216 can be periodic, sustained, for a predefined period of time, etc. In some examples, the EMG sensors 142 send the EMG signals 206 to the EMS controller 138 during electrical stimulation of the muscles via the electrical current provided by the EMS source 136. In such examples, the analyzer 208 analyzes the EMG data 206 to confirm, for example, that the muscles are being activated and/or to track changes in electrical activity indicative of, for example, muscle fatigue. In some examples, the analyzer 208, the EMG sensors 142, the EMG controller 138, and the EMS source 136 form a feedback loop to control the muscle stimulation. In some examples, the body movement sensor(s) 140 and the data they produce are used in the same or another feedback loop to control a position of the body part being assisted.

In the example of FIG. 2, if the analyzer 208 determines that the user 104 intends to move one or more of this body parts, the analyzer 208 also communicates with a pump activator 218. Based on the data received from the analyzer 208, the pump activator 218 generates one or more vacuum pump instructions 220 and transmits the instructions 220 to the pump controller 124 of the WAD 102 (e.g., via a wired or wireless connection). The pump controller 124 may instruct the vacuum pump 120 to evacuate air from the jamming actuator(s) 108, 110, 112, 114 and/or to pump air into the jamming actuator(s) depending on the instructions 220. As explained above, should support of a joint or limb be intended, the vacuum pump 120 selectively removes air from one or more of the jamming actuator(s) 108, 110, 112, 114 via the respective vacuum pump hose(s) 126, 127, 129, 131, 133, 135 based on the location of the jamming actuator(s) 108, 110, 112, 114 relative to the body parts that the user intends to use and/or are being electrically stimulated (e.g., as determined by the analyzer 208).

The analyzer 208 communicates with the EMS activator 212 and the pump activator 218 to coordinate stiffening of the jamming actuator(s) 108, 110, 112, 114 with electrical stimulation of the muscle(s) via delivery of the electrical current 216 to the EMS electrodes 134. In some examples, the analyzer 208 communicates with the EMS activator 212 and the pump activator 218 at substantially the same time such that the pump activator 218 sends the instructions 220 to the pump controller 124 at substantially the same time as the EMS activator 212 sends the EMS instructions 214 to the EMS source 136. In other examples, the analyzer 208 waits to receive the EMG signal data 142 from the EMG sensors 142 that indicates that the muscles are being stimulated via the electrical current 216 before communicating with the pump activator 218. In such examples, the pump activator 218 sends the vacuum pump instructions 220 to the pump controller 124 after the EMS activator 212 sends the EMS instructions 214 to the EMS source 136 and the muscles are activated. As a result, the stiffening of the jamming actuator(s) 108, 110, 112, 114 occurs after the muscles have been stimulated (e.g., seconds after the electrical current 216 is applied to the muscles). Thus, in such examples, the electrical stimulation of the muscles (e.g., as reflected in the EMG data 206) is a trigger for stiffening of the jamming actuator(s) 108, 110, 112, 114.

In other examples, the analyzer 208 communicates with the pump activator 218 based on, for example, the data 200, 206 received from the body movement detection sensor(s) 140 and/or the EMG sensors 142 and before communicating with the EMS activator 212. In some such examples, the analyzer 208 instructs the pump activator 218 to activate the vacuum pump 120 before the electrical current 216 is delivered to the EMS electrodes 134. For example, it may take a longer time for the jamming actuator(s) 108, 110, 112, 114 to stiffen than for the electrical current to be delivered to the EMS electrodes 134 to stimulate the user's muscles. In such examples, the analyzer 208 may instruct the vacuum pump 120 to begin to stiffen the jamming actuator(s) 108, 110, 112, 114 before the electrical current 216 is delivered so that when the muscle(s) are stimulated, the jamming actuator(s) 108, 110, 112, 114 are already in, or moving toward, a substantially rigid state to support the user's body part(s). Thus, in some examples, the data 200, 206 indicative of body movement and/or muscle activity (e.g., prior to electrical stimulation) is a trigger for stiffening of the jamming actuator(s) 108, 110, 112, 114.

When the user 104 wishes to release one or more body parts that are being supported by the jamming actuator(s) 108, 110, 112, 114, the user 104 can perform a voluntary movement to indicate that the user no longer wishes to maintain the selected limb position. For example, the user 104 can push his arm down from a raised position toward a lowered position (e.g., relative to the ground). In the example of FIG. 2, the body movement detection sensor(s) 140 detect movement of the arm to the lowered position and send signals 200 to the EMS controller 138 carrying data indicating the change in position of the arm. As another example, the user 104 can disengage contact with an object he or she is holding in his hand, such as a cup. The body movement detection sensor(s) 140 detect a pressure change at the user's hand and send the corresponding signal data 200 to the EMS controller 138. In some examples, the change in limb position is caused by a mechanical device, such as a cable or pneumatic actuator.

In some examples, the EMG sensors 142 send EMG data 206 to the EMS controller 138 that can indicate changes in electrical activity of the muscles, such as electrical activity generated as a result of the user attempting to release his fingers from a gripping an object.

The example analyzer 208 analyzes the data 200, 206 to determine whether the jamming actuator(s) 108, 110, 112, 114 should be softened to release a corresponding body part. For example, if the user 104 is gripping an object with his hand and if the analyzer 208 determines that the user 104 no longer wishes to maintain the grip, the analyzer 208 sends a message to the EMS activator 212 to, for example stimulate the user's finger muscles to cause the user's hand to open via the electrical current 216 from the EMS source 136. Also, the analyzer 208 sends a message to the pump activator 218 that the jamming actuator(s) 108, 110, 112, 114 should be released (e.g., softened). The pump activator 218 sends vacuum pump instructions 220 to the pump controller 124 to direct the vacuum pump 120 to deliver air to the jamming actuator(s) 108, 110, 112, 114 to soften the actuators. When the jamming actuator(s) 108, 110, 112, 114 are softened, the jamming actuator(s) 108, 110, 112, 114 no longer hold the hand in the grip position. Thus, the object is released.

Thus, the example EMS controller 138 of FIG. 2 is constructed to selectively activate, for example, electrical stimulation of the user's muscles (e.g., via the EMS source 136 and the EMG electrodes 142) and/or to selectively stiffen the jamming actuators 108, 110, 112, 114 (e.g., via the vacuum pump 120) based on user intent with respect to positioning of one or more of his body parts. The EMS controller 138 responds to, for example, voluntary movements by the user 104 to initiate electrical stimulation of the muscles and/or stiffening of the jamming actuator(s). The EMS controller 138 also responds to decisions by the user 104 to change or release assisted body part(s) by softening of the jamming actuator(s) and/or electrical stimulation of the muscles (e.g., to cause the user's hand to open).

Figure 3:
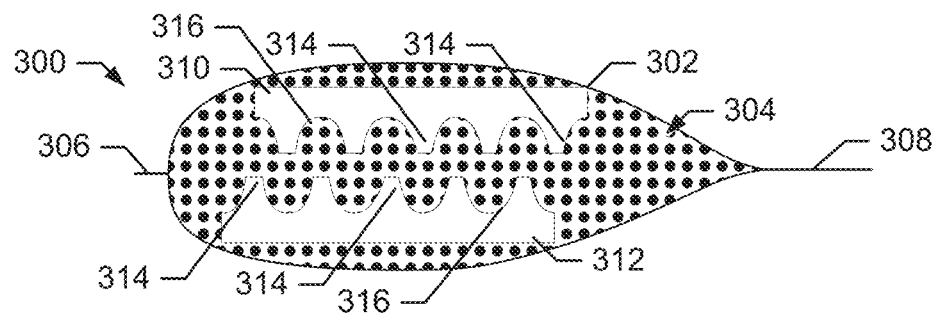
FIG. 3 is a cross-sectional view of an example jamming actuator constructed in accordance with teachings disclosed herein.

FIG. 3 is a cross-sectional view of a first example jamming actuator 300. The first example jamming actuator 300 can implement one or more of the jamming actuators 108, 110, 112, 114 of the example WAD 102 of FIGS. 1A, 1B, and/or 2 and/or form a portion of one or more of the jamming actuators 108, 110, 112, 114 of FIGS. 1A, 1B, and/or 2. The example jamming actuator 300 includes an elastomeric membrane 302 that forms a housing or enclosure for solid particles 304. The membrane 302 can include rubber (e.g., a latex rubber) or a soft nonporous fabric. The solid particles 304 can be, for example, grains such as sand, diatomaceous earth, etc. In the example of FIG. 3, a portion of the membrane 302 forms an anchor 306 for coupling the first example jamming actuator 300 to, for example, the frame 106 of the WAD 102. The first example jamming actuator 300 of FIG. 3 includes a connector 308 for coupling to a vacuum pump hose (e.g., the vacuum pump hose 126, 127, 129, 131, 133, 135 of FIGS. 1A, 1B, and/or 2) of a vacuum pump (e.g., the vacuum pump 120 of FIGS. 1A, 1B, and/or 2).

As disclosed above, forces generated by the jamming actuator 300 can be affected by, for example, a strength of the vacuum created by the vacuum pump to which the jamming actuator 300 is coupled or a thickness of the solid particles 304 disposed in the elastomeric membrane 302. In the context of a wearable device such as the WAD 102, some of the jamming actuators may be required to support limbs such as user's arm, leg, etc. and, thus, must generate sufficient forces to support heavier limbs. However, increasing a power of the vacuum pump can increase a weight of the vacuum pump that is carried by the user 104 of the WAD 102, thereby affecting the ease of portability of the WAD 102. Also, increasing a size of the solid particles 304 or an amount of the solid particles 304 disposed in the membrane 302 can increase a weight and/or a form factor of the WAD 102 and, thus, make the WAD 102 more cumbersome and/or less comfortable for the user 104 to wear when the jamming actuators are in the softened state and/or the substantially rigid state.

To reduce a volume of the solid particles 304 in the membrane 302 and/or a vacuum pump strength while enabling the first example jamming actuator 300 to generate sufficient forces to support the user's limbs, the example jamming actuator 300 of FIG. 3 includes a first interlocking portion 310 and a second interlocking portion 312. The first and second interlocking portions 310, 312 are made of a rubber material having increased rigidity as compared to, for example, a rubber material used to form the membrane 302. As illustrated in FIG. 3, each of the first and second interlocking portions 310, 312 of this example include a plurality of teeth 314 and a plurality of grooves 316 disposed between the teeth 314. In the example of FIG. 3, when the jamming actuator 300 stiffens as a result of the removal of air from the membrane 302, the teeth 314 of the first and second interlocking portions 310, 312 interlock and/or mesh via the grooves 316.

Thus, under vacuum, the enmeshing portions 310, 312 interact (e.g., enmesh or lock) to form a substantially stiff structure that, along with the jamming of the solid particles 304, transforms or transitions the jamming actuator 300 to a rigid or a substantially rigid state. When the jamming actuator 300 is substantially rigid, the jamming actuator 300 can be used to support one or more body parts of the user 104 of the WAD 102 as disclosed above. The enmeshing portions 310, 312 enable smaller solid particle 304 and/or reduced vacuum forces to be used as compared to if the solid particles 304 were used alone (e.g., only granular jamming without the presence of the enmeshing members 310, 312). The interlocking portions 310, 312 also provide structure to the membrane 302 when the membrane 302 is in a softened state that the user 104 may find more comfortable to wear as compared to if the membrane were filled with solid particles 304 alone. Thus, the enmeshing portions 310, 312 of the example jamming actuator 300 of FIG. 3 improves wearability of the jamming actuator 300 while allowing the jamming actuator 300 to generate sufficient forces to support the user's body part(s) when stiffened.

Figure 4:
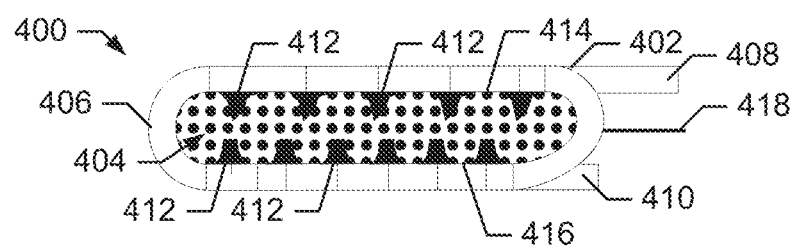
FIG. 4 is a cross-sectional view of an example jamming actuator constructed in accordance with the teachings of this disclosure.

FIG. 4 is a cross-sectional view of a second example jamming actuator 400. The second example jamming actuator 400 can implement one or more of the jamming actuators 108, 110, 112, 114 of the example WAD 102 of FIGS. 1A, 1B, and 2 and/or form a portion of one or more of the jamming actuators 108, 110, 112, 114 of FIGS. 1A, 1B, and/or 2.

Figure 5:
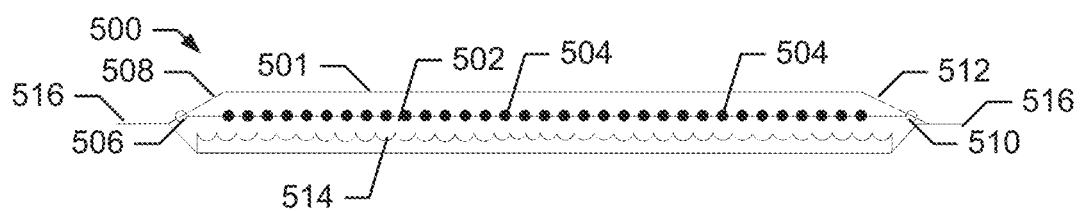
FIG. 5 is a cross-sectional view of an example jamming actuator constructed in accordance with the teachings of this disclosure.

The example jamming actuator 400 of FIG. 4 includes an elastomeric membrane 402 (e.g., a soft rubber). Solid particles 404 (e.g., grains) are disposed in the membrane 402. The example membrane 402 of FIG. 4 includes a first anchor 406, a second anchor 408, and a third anchor 410. The first, second, and third anchors 406, 408, 410 can be used to couple the example jamming actuator 400 to, for example, the frame 106 of the WAD 102. As shown in FIG. 5, the example jamming actuator 400 of FIG. 4 includes a plurality of teeth 412 disposed in the membrane 402. The teeth 412 are formed from, for example, a rubber having an increased hardness as compared to a rubber used to form the elastomeric membrane 402. In this example, a first plurality of teeth 412 are coupled to a first wall 414 of the membrane 402 (e.g., on the interior of the membrane), where each of the teeth 412 are spaced apart from one another along the first wall 414. A second plurality of teeth 412 are coupled to a second wall 416 of the membrane 402 of FIG. 4 opposite the first wall 414, where each of the second teeth 412 are spaced apart from one another along the second wall 416. The example jamming actuator 400 also includes a connector 418 for coupling with, for example, a vacuum pump hose.

In the example jamming actuator 400 of FIG. 4, one or more of the anchors 406, 408, 410 of the elastomeric membrane 402 can be pulled or stretched by, for example movement of a body part proximate to the jamming actuator 400. For example, the jamming actuator 400 of FIG. 4 can be coupled to the WAD 102 near the user's wrist joint. When the user 104 bends his or her wrist (e.g., toward the ground), the second anchor 408 is stretched. The stretching of the second anchor 408 causes the first wall 414 of the membrane 402 to stretch, which can align the first plurality of teeth 412 with the spaces formed between the second plurality of teeth 412 at the second wall 416. When a vacuum is applied to the jamming actuator of FIG. 4, the respective first and second pluralities of teeth interweave and/or clamp together. Also, the solid particles 404 jam together as a result of the vacuum. Thus, the example jamming actuator 400 stiffens or assumes a substantially rigid state. In the example of FIG. 4, the coupling of the teeth 412 to the walls of the membrane 402 efficiently uses the real estate of the membrane 402 while providing an interlocking structure that reduces, for example, the amount of solid particles 404 and/or vacuum strength employed to stiffen the actuator to sufficiently support the user's limb.

FIG. 5 is a cross-sectional view of a third example jamming actuator 500. The third example jamming actuator 500 can implement one or more of the jamming actuators 108, 110, 112, 114 of the example WAD 102 of FIGS. 1A, 1B, and 2 and/or form a portion of one or more of the jamming actuators 108, 110, 112, 114 of FIGS. 1A, 1B, and/or 2.

The third example jamming actuator 500 of the illustrated example includes an elastomeric membrane 501. In the example of FIG. 5, the membrane 501 may be wrapped around one or more body parts of the user to form an envelope around the same. The example jamming actuator 500 of FIG. 5 includes a string or wire 502 including solid particles 504 coupled to the string 502. In the example of FIGS. 5A and 5B, the solid particles 504 have a substantially spherical shape. A first end 506 of the string 502 is coupled to a first end 508 of the membrane 501 and a second end 510 of the string 502 is coupled to a second end 512 of the membrane 501. The example jamming actuator 500 includes a plurality of sockets 514. The sockets 514 can be formed from, for example, rubber, and/or can be sized to receive the respective solid particles 504. The example jamming actuator 500 can include a plurality of strings 502 of solid particles 504 and/or sockets 514 to receive the solid particles 504 of the string(s) 502. The example jamming actuator 500 includes anchors 516 for coupling the jamming actuator 500 to the WAD 102.

When the example jamming actuator 500 of FIG. 5 is exposed to a vacuum, the solid particles 504 of the string 502 interlock with the respective sockets 514. The interlocking of the solid particles 504 with the sockets 514 provides rigidity to the jamming actuator 500. The string(s) 502 serve as reinforcements to increase strength of the stiffened membrane 501. The arrangement of the solid particles 504 along the string(s) 502 provides for substantially uniform stiffness along the length of the membrane 501. Thus, the example jamming actuator 500 of FIG. 5 can be used to support larger joints such as the user's shoulder or elbow where a jamming actuator having a membrane with a longer length can be used for support of the larger joint (as compared to, e.g., the user's knuckle joint).

Figure 6:
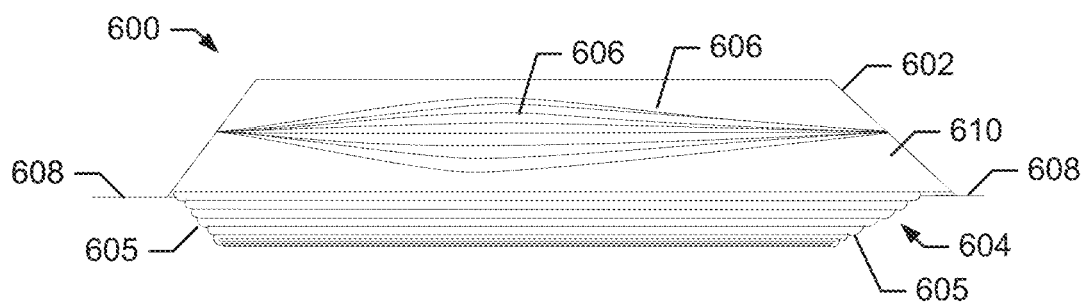
FIG. 6 is a perspective view of an example jamming actuator constructed in accordance with the teachings disclosed herein.

FIG. 6 is a perspective view of a fourth example jamming actuator 600. The fourth example jamming actuator 600 can implement one or more of the jamming actuators 108, 110, 112, 114 of the example WAD 102 of FIGS. 1A, 1B, and 2 and/or form a portion of one or more of the jamming actuators 108, 110, 112, 114 of FIGS. 1A, 1B, and/or 2.

The example jamming actuator 600 of FIG. 6 includes an elastomeric membrane 602. The example jamming actuator 600 includes a first or upper membrane 602 and a second or lower membrane 604. The second membrane 604 includes a plurality of ribs 605. The first and second membranes 602, 604 may be wrapped around one or more body parts of the user to form an envelope around the same. The first and second membranes 602, 604 can include, for example, elastomeric or non-porous fabric sheets.

The example jamming actuator 600 of FIGS. 6A and 6B includes one or more strings or wires 606. In some examples, two or more of the strings 606 at least partially overlap or form a bundle. The first and second membranes 602, 604 enclose the string(s) 606 in an envelope. The jamming actuator 600 includes anchors 608 for coupling the jamming actuator 600 to the WAD 102.

In the example of FIG. 6, when a vacuum is applied to the jamming actuator 600 (e.g., via a vacuum pump line), the first and second membranes 602, 604 press against one another. Also, when the vacuum is applied, the strings 606 sink into wells formed by ribs 605 of the second membrane 604. Thus, the string(s) 606 can sink into different areas of the second membrane 604 based on, for example, the number of strings, the number of ribs 605, etc. The strings 606 serve as reinforcements to increase strength of the stiffened membranes 602, 604 as compared to, for example, stiffening of the membrane 602, 604 alone. Thus, the jamming actuator 600 transitions into a substantially rigid envelope that can be used to support one or more body parts without the use of granular particles.

As disclosed above, one or more jamming actuators are worn about a body part of the user, such as the user's finger, arm, shoulder, etc. FIGS. 7A, 7B, 8A, 8B, 9A, 9B, 10A, 10B, 11A, and 11B illustrate different example jamming actuators. For illustrative purposes, the example jamming actuators of FIGS. 7A, 7B, 8A, 8B, 9A, 9B, 10A, 10B, 11A, and 11B are shown as worn on the user's finger. However, the example jamming actuators of FIGS. 7A, 7B, 8A, 8B, 9A, 9B, 10A, 10B, 11A, and 11B or portions thereof could be worn about other body parts as well (e.g., the user's elbow). Also, although FIGS. 7A, 7B, 8A, 8B, 9A, 9B, 10A, 10B, 11A, and 11B illustrate two jamming actuator worn on the user's finger (e.g., at the proximal interphalangeal joint (i.e., the knuckle) and the distal interphalangeal joint), in other examples, only one of the example jamming actuators is worn at the user's finger.

FIGS. 7A and 7B are cross-sectional views of a fifth example jamming actuator 700a, 700b shown worn on a finger 702 of the user 104 of FIGS. 1A and 1B. Each of the example jamming actuators 700a, 700b of FIGS. 7A and 7B include at least two overlapping membrane envelopes 704 such that the envelopes 704 form pleats. The envelopes 704 can be formed from, for example, a non-porous fabric or rubber. In some examples, the envelopes 704 include solid particles, teeth, strings, solid particles coupled to a string, etc. disposed inside the envelopes as substantially disclosed above with respect to FIGS. 3-6. As shown in FIGS. 7A and 7B, a vacuum pump line 706 is coupled to the jamming actuators 700a, 700b to remove or deliver air to the jamming actuators 700a, 700b.

FIG. 7A illustrates the user's finger 702 in a relaxed position. FIG. 7B illustrates the user's finger 702 in an active position to, for example, grasp an object. In the example of FIG. 7B, the user may have voluntarily moved (e.g. pushed) his fingertip 708 down so as to partially bend his finger 702. As illustrated in FIG. 7B, movement of the fingertip 708 downward causes the pleated envelopes 704 of the jamming actuator 700b proximate to the user's fingertip to expand along the fingertip 708. As a result of the downward movement of the fingertip 708, a knuckle 710 of the user's finger 702 may bend upward.

Movement of the user's fingertip 708 can trigger electrical stimulation of the finger muscles as disclosed above with respect to the example WAD 102 and the EMS controller 138 of FIGS. 1A, 1B, and/or 2. The movement of the fingertip 708 and/or electrical stimulation of the finger muscles can trigger jamming of the example jamming actuators 700a, 700b (e.g., via communication between the pump controller 124 and the EMS controller 138 as disclosed above in connection with FIGS. 1A, 1B, and/or 2). In the example of FIGS. 7A and 7B, removal of air from the envelopes 704 of the jamming actuator 700a proximate to the user's knuckle 710 transforms the jamming actuator 700a into a rigid or stiff structure to support the user's finger 702 at the knuckle 710 (e.g., in the upwardly bent position). Also, removal of air from the envelopes 704 of the jamming actuator 700b proximate to the user's fingertip 708 transforms the jamming actuator 700b into a rigid structure to force the fingertip 708 into a gripping position that will resist an object's counterforce when the hand grips the same to hold the fingertip 708 downward in the gripping position. The extended or pleated envelopes 704 of the jamming actuators 700a, 700b support the user's finger 702 between the knuckle and the fingertip 708. The extended envelopes 704 help hold the user's fingertip 708 in the bent position by increasing an area of the user's finger 702 over which the jamming actuator 700b supports the finger. Thus, the jamming actuator 700a, 700b enable forces to be transferred from the muscles of the user's finger 702 to the jamming actuators 700a, 700b to support the finger 702 in the active position.

FIGS. 8A and 8B are cross-sectional views of a sixth example jamming actuator 800a, 800b worn on the finger 702 of the user 104. Each of the example jamming actuators 800a, 800b of FIGS. 8A and 8B includes an elastomeric or fabric membrane envelope 802. Each of the membrane envelopes 802 includes a rack 804 having teeth 806. Also, each of the membrane envelopes 802 includes a ring 808. The racks 804 and the ring 808 can be made from, for example, rubber. In some examples, the membrane envelopes 802 also include solid particles (e.g., grains).

As illustrated in FIGS. 8A and 8B, each of the rings 808 engages with the teeth 806 of the respective racks 804 such that the rings 808 and the racks 804 form a ratchet. As shown in FIG. 8B, when the user 104 bends his fingertip 708, the ring 808 slides along the teeth 806 of the rack 804 of the jamming actuator 800b proximate to the fingertip 708. Also, the ring 808 of the jamming actuator 800a proximate to the knuckle 710 slides along the teeth 806 of the rack 804. When a vacuum is applied to the jamming actuators 800a, 800b, the jamming actuators 800a, 800b stiffen, which causes the rings 808 to engage with the respective ones of the teeth 806 (e.g., with a groove between two teeth 806) of the jamming actuators 900a, 900b and prevents further sliding of the rings 808 along the racks 804. The engagement of the rings 808 with the teeth 806 of the racks 804 provides additional structural support to the jamming actuators 800a, 800b to help hold the finger 702 in place. Also, the engagement of the rings 808 with the teeth 806 at predefined positions along the respective racks 804 provides for fine-tuned positioning and support of, for example, the fingertip 708 and/or the knuckle 710 at an angle selected by the user 104. Thus, the example jamming actuators 800a, 800b of FIGS. 8A and 8B provide for increased control over a position at which the finger 702 is held by the jamming actuators 800a, 800b. The softening of the jamming actuators 800a, 800b enables the rings 808 to move out of engagement with the teeth 806 for further positioning of the finger 702 or to rest the finger 702.

FIGS. 9A and 9B are cross-sectional views of a seventh example jamming actuator 900a, 900b worn on the finger 702 of the user 104. Each of example jamming actuators 900a, 900b of FIGS. 9A and 9B includes an elastomeric or fabric membrane 902. Each of the membranes 902 includes a gear 904 having teeth 906. Also, each of the membranes 902 includes a pawl 908 (e.g., coupled to wall of the membrane 902) to engage with the teeth 906. The gear 904 and the pawl 908 can be made of, for example, rubber.

In the examples of FIGS. 9A and 9B, when the user 104 bends his fingertip 708, the gear 904 of the jamming actuator 900b proximate to the user's fingertip 708 rotates, as represented by the arrow 910 in FIG. 9B. The rotation of the gear 904 of the jamming actuator 900b causes the teeth 906 to move (e.g., slide) past the pawl 908. Also, the gear 904 of the jamming actuator 900a proximate to the knuckle 710 rotates as a result of the knuckle bending, which causes the teeth 906 to move (e.g., slide) past the pawl 908. When a vacuum is applied to the jamming actuators 900a, 900b, the jamming actuators 900a, 900b stiffen, which causes the pawls 908 to engage with the respective ones of the teeth 906 (e.g., with a groove between two teeth 906) of the jamming actuators 900a, 900b and prevents rotation of the gears 904. The engagement of the pawls 908 with the teeth 906 of the gears 904 provides additional structural support to the jamming actuators 900a, 900b to help hold the finger 702 in place. Also, the engagement of the pawl 908 with the teeth 906 at predefined positions along the respective gears 904 provides for fine-tuned positioning and support of, for example, the fingertip 708 at the bent angle selected by the user 104. As disclosed above, forces generated by the user's muscles to hold the fingertip 708 in the selected position are transferred to the jamming actuators 900a, 900b.

The example jamming actuators 900a, 900b of FIGS. 9A and 9B can also be used, for example, at the elbow joint of user 104. For example, the rotating gears 904 of the jamming actuators 900a, 900b can replace rotational joints typically found in arm braces that allow for bending of the elbow. A WAD 102 including the jamming actuator(s) 900a, 900b of FIGS. 9A and 9B at the elbow joint can enable flexion and/or extension of the elbow via the rotation of the gears 904 when the jamming actuator(s) 900a, 900b are relaxed and temporary locking the joint at the selected angle when the jamming actuator(s) 900a, 900b are stiffened. For example, when the actuators are softened, the pawls 908 can move out of engagement with the teeth 906 (e.g., via a springing force associated with the pawl 908).

FIGS. 10A and 10B are cross-sectional views of an eighth example jamming actuator 1000 worn on the finger 702 of the user 104. The example jamming actuator 1000 of FIGS. 10A and 10B includes one or more elastomeric envelopes 1002. In some examples, the envelopes 1002 extend substantially along the length of the finger 702. In other examples, the envelopes 1002 cover only a portion of the user's finger 702.

The envelopes 1002 include solid particles 1004 (e.g., grains) disposed therein. In some examples, the solid particles 1004 are coupled to a string or wire 1006 (e.g., as disclosed above in connection with the third example jamming actuator 500 of FIG. 5). In the examples of FIGS. 10A and 10B, the solid particles 1004 are spherical and substantially rigid. The envelopes 1002 can include elastomeric indentations 1008 to receive the solid particles 1004. The solid particles 1004 can rotate within the indentations 1008 (e.g., similar to a ball joint) when the user 104 bends, for example, his fingertip 708. When a vacuum is applied to the example actuator 1000, the jamming actuator 1000 stiffens and the indentations 1008 of the envelopes 1002 hold the solid particles 1004.

In some examples, the envelopes 1002 include elastomeric pockets 1010 coupled to supports 1012. As illustrated in FIG. 10A, the pockets 1010 can be spherically shaped and receive solid particles 1004 therein. The supports 1012 can be formed from, for example, a rubber material having a greater hardness than a rubber material from which the pockets are formed. The solid particles 1004 disposed in the pockets 1010 and rotate therein similar to a ball joint.

The example jamming actuator 1000 of FIGS. 10A and 10B enables the amount of support provided by the jamming actuator 1000 over the length of the finger 702 to be customized based on the number and/or size (e.g., length) of the envelopes 1002. As shown in FIGS. 10A and 10B, the envelopes 1002 of the example jamming actuator 1000 of FIGS. 10A and 10B can cover jointed (e.g., the knuckle 710, the fingertip 708) and non-jointed portions (e.g., the portion of finger 702 between the knuckle 710 and the fingertip 708) of the user's finger 702 to provide additional support of the user's finger 702. In other examples, the example jamming actuator 1000 only includes the envelopes 1002 at the finger joints. The ability of the ball-shaped solid particles to rotate within the indentations 1008 and/or the pockets 1010 allows for a user to move (e.g., bend) his finger with ease to a desired position.

FIGS. 11A and 11B are cross-sectional views of a ninth example jamming actuator 1100 worn on the finger 702 of the user 104. The example jamming actuator 1100 of FIGS. 11A and 11B includes one or more rings 1102 that wrap around one or more portions of the user's finger 702. The rings 1102 can include a fabric, a rubber, etc. The example jamming actuator 1100 includes one or more vacuum lines 1104. The vacuum lines 1104 extends along the length of the user's finger 702 between the rings 1102. The example jamming actuator 1100 includes one or more elastomeric pockets 1106 coupled to the vacuum lines 1104. The pockets 1106 can be spherically shaped. One or more solid particles 1108 are disposed in the pockets 1106. The rings 1102 facilitate placement of the solid particles 1108, the pockets 1106, and the vacuum lines 1104.

When a vacuum is applied to the example actuator 1100 of FIGS. 11A and 11B, the vacuum lines 1104 remove fluid (e.g., air) from the pockets 1106 to stiffen the jamming actuator 1100 and enable the jamming actuator 1100 to support the user's finger. In some examples, the respective pockets 1106 include one or more holes through which the air is removed from the pockets 1106 via the vacuum lines 1104. The example jamming actuator 1100 of FIGS. 11A and 11B provides for support of the user's finger 702 (or other body part) without use of an envelope to substantially surround the finger 702.

While an example manner of implementing the example WAD 102 and the example EMS controller 138 is illustrated in FIGS. 1A, 1B, and/or 2, one or more of the elements, processes and/or devices illustrated in FIGS. 1A, 1B, and/or 2 may be combined, divided, re-arranged, omitted, eliminated and/or implemented in any other way. Further, the example pump controller 124, the example body movement detection sensor(s) 140, the example EMS electrodes 134, the example EMS source 136, the example EMG sensors 142, the example sensor data collector 202, the example database 204, the example analyzer 208, the example EMS activator 212, the example pump activator 218 and/or, more generally, the example system 100 of FIGS. 1A, 1B, and/or 2 may be implemented by hardware, software, firmware and/or any combination of hardware, software and/or firmware. Thus, for example, any of the example pump controller 124, the example body movement detection sensor(s) 140, the example EMS electrodes 134, the example EMS source 136, the example EMG sensors 142, the example sensor data collector 202, the example database 204, the example analyzer 208, the example EMS activator 212, the example pump activator 218 and/or, more generally, the example system 100 of FIGS. 1A, 1B, and/or 2 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example pump controller 124, the example body movement detection sensor(s) 140, the example EMS electrodes 134, the example EMS source 136, the example EMG sensors 142, the example sensor data collector 202, the example database 204, the example analyzer 208, the example EMS activator 212, the example pump activator 218 and/or, more generally, the example system 100 of FIGS. 1A, 1B, and/or 2 is/are hereby expressly defined to include a non-transitory computer readable storage device or storage disk such as a memory, a digital versatile disk (DVD), a compact disk (CD), a Blu-ray disk, etc. storing the software and/or firmware. Further still, the example system 100 of FIGS. 1A, 1B, and/or 2 may include one or more elements, processes and/or devices in addition to, or instead of, those illustrated in FIGS. 1A, 1B, and/or 2, and/or may include more than one of any or all of the illustrated elements, processes and devices.

Figure 12:
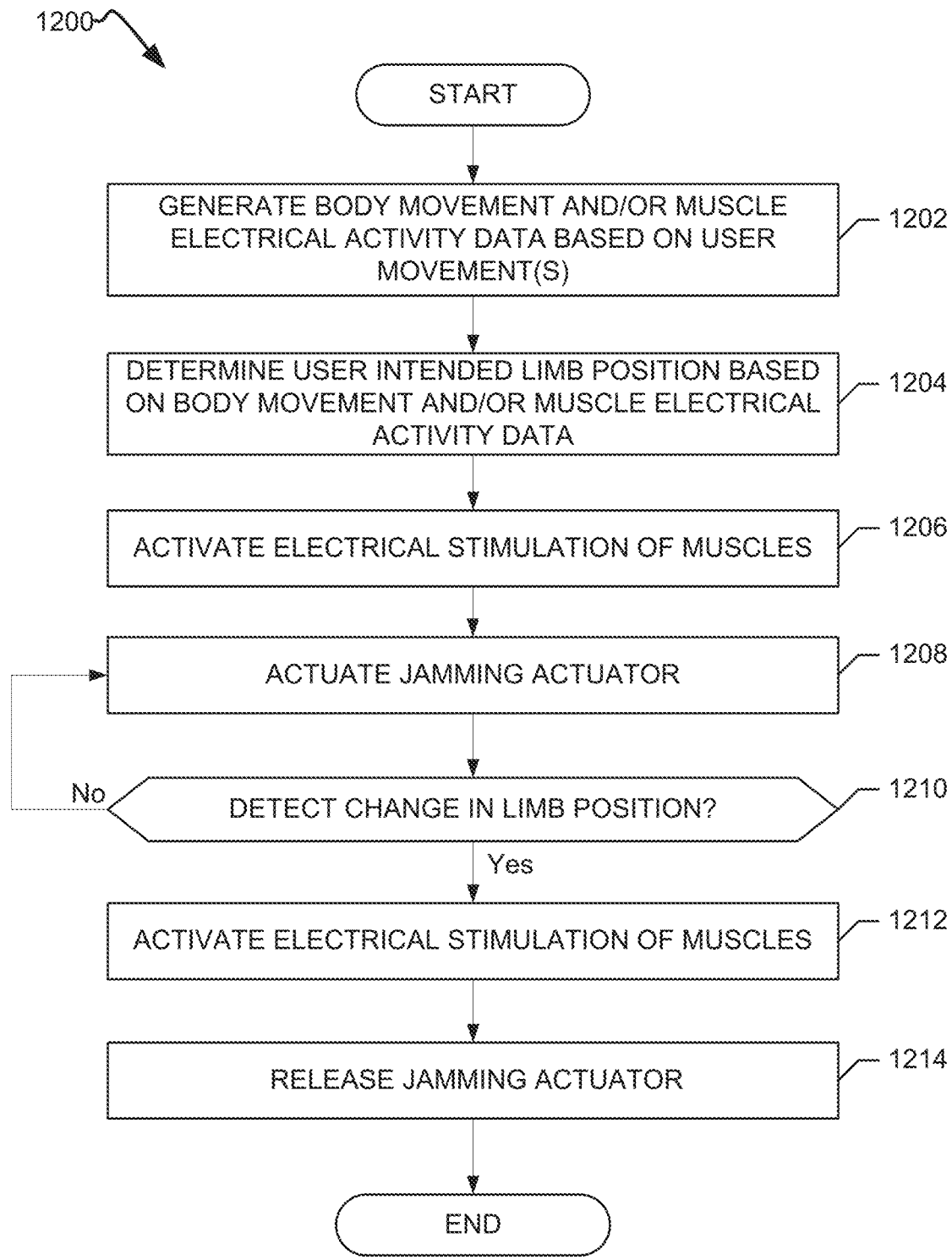
FIG. 12 is a flowchart representative of example machine readable instructions that may be executed to implement the example system of FIGS. 1 and/or 2.

A flowchart representative of example machine readable instructions which may be executed to implement the example system 100 and/or components thereof illustrated in FIGS. 1A, 1B, and/or 2 is shown in FIG. 12. In this example, the machine readable instructions comprise a program for execution by a processor such as the processor 138 shown in the example processor platform 1300 discussed below in connection with FIG. 13. The program may be embodied in software stored on a tangible computer readable storage medium such as a CD-ROM, a floppy disk, a hard drive, a digital versatile disk (DVD), a Blu-ray disk, or a memory associated with the processor 138, but the entire program and/or parts thereof could alternatively be executed by a device other than the processor 138 (e.g., the pump controller 124 of FIGS. 1A, 1B, and/or 2) and/or embodied in firmware or dedicated hardware. Further, although the example program is described with reference to the flowchart illustrated in FIG. 12, many other methods of implementing the example system 100 may alternatively be used. For example, the order of execution of the blocks may be changed, and/or some of the blocks described may be changed, eliminated, or combined.

As mentioned above, the example process of FIG. 12 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 12 is a flowchart representative of example machine-readable instructions that, when executed, cause the example system 100 of FIGS. 1A, 1B, and/or 2 to actuate the jamming actuator(s) 108, 110, 112, 114 of example WAD 102 to support one or more body parts of the user 104 who is wearing the WAD 102 in a selected limb position. The jamming actuator(s) 108, 110, 112, 114 of example WAD 102 can include any of the example jamming actuators 300, 400, 500, 600, 700, 800, 900, 1000, 1100 of FIGS. 3-6, 7A, 7B, 8A, 8B, 9A, 9B, 10A, 10B, 11A and/or 11B. In some examples, the WAD 102 includes different ones of the jamming actuators 300, 400, 500, 600, 700, 800, 900, 1000, 1100 of FIGS. 3-6, 7A, 7B, 8A, 8B, 9A, 9B, 10A, 10B, 11A and/or 11B based on, for example, the position of the jamming actuators relative to the user's body parts. For example, the rotating ratchet of the example jamming actuator 900a, 900b of FIGS. 9A and 9B can be used at the elbow joint and the pleated envelopes of the example jamming actuator 700a, 700b of FIGS. 7A and 7B can be used at the finger joints. Other combinations of jamming actuators are possible. In the example of FIG. 12, the body parts can include, for example, the user's arm, hand, fingers, etc. The example instructions of FIG. 12 can be executed by the EMS controller 138 of FIGS. 1A, 1B, and/or 2. One or more of the instructions can be executed by the pump controller 124 of FIGS. 1A, 1B, and/or 2.

In the example of FIG. 12, the body movement detection sensor(s) 140 of the WAD 102 detect, for example, a movement, a change in position, a change in contact pressure, etc. of one or more body parts of the user. For example, the body movement detection sensor(s) 140 detect if the user 104 has performed a voluntary movement such as raising his or her arm. Also, the EMG electrodes 142 detect electrical activity of the muscles, such as a contraction of the user's hand muscles as a result of the user 104 voluntarily squeezing his or her hand. The example body movement detection sensor(s) 140 and/or the EMG sensors 142 generate data (e.g., the data 200, 206) indicative of the body movements and/or the electrical activity of the muscles (block 1202).

The example EMS controller 138 determines an intended limb movement and/or position based on the body movement and/or muscle electrical activity signal data received from the body movement detection sensor(s) 140 and/or the EMG sensors 142 (block 1204). For example, the sensor data collector 202 of the EMS controller 138 processes the data 200, 206 for analysis by the analyzer 208. The example analyzer 208 applies one or more rules 210 stored in the database 204 to determine the user's intent. For example, if the electrical activity of an arm muscle exceeds a duration threshold and/or a threshold amplitude, the analyzer 208 determines that the user 104 intends to raise his arm. As another example, if the signal data indicating a change in position exceeds a predefined threshold in a correct polarity (e.g., upward motion as opposed to downward motion), the analyzer 208 determines that the user 104 intends to lift his arm (as compared to anomalous data indicating, for example, an involuntary movement).

If the example analyzer 208 determines that the user intends to move one or more of his body parts to assume a desired limb position, the example analyzer 208 sends a message to the EMS activator 212 of the example EMS controller 138. The EMS activator 212 sends one or more instructions 214 to the EMS source 136 to send electrical current 216 to the EMS electrodes 134 attached to the user's skin (e.g., at the first, second, and/or third stimulation sites 128, 130, 132) (block 1206). The switching circuit 139 of the EMS source selectively connects one or more of the EMS electrodes 134 to the battery pack 137 to deliver current to the same. The application of the electrical current 216 to user's muscles causes the muscles to contract to enable, for example, the user to hold his or her arm in a lifted position and/or to grasp an object with his hand.

In the example of FIG. 12, electrical stimulation the user's muscles is a trigger for one or more of the jamming actuators 108, 110, 112, 114 of the WAD 102 to be actuated (block 1208). For example, the analyzer 208 sends a message to the pump activator 218 of the example EMS controller 138. The pump activator 218 sends one or more instructions 220 to the pump controller 124 of the vacuum pump 120 of the WAD 102. The vacuum pump 120 applies a vacuum to the jamming actuator(s) 108, 110, 112, 114 via the vacuum pump hose(s) 126, 127, 129, 131, 133, 135 to cause the jamming actuator(s) 108, 110, 112, 114 to stiffen. In some examples, the pump controller 124 and/or the EMS controller 138 selectively instructs the jamming actuator(s) 108, 110, 112, 114 to actuate based on, for example the location of the jamming actuator(s) 108, 110, 112, 114 relative to the muscles being stimulated by the electrical current 216.

If the example body movement detection sensor(s) 140 and/or the EMG sensor(s) 142 detect a change in limb position as a result of, for example, a voluntary movement by the user 104, the example analyzer 208 determines that the user 104 no longer wishes to maintain the selected limb position (e.g., the user pushes his or her arm down as an indication that the user 104 no longer wishes to have his arm raised) (block 1210). In such examples, the EMS activator 212 instructs the EMS source to deliver the electrical current 216 to EMS electrodes to, for example, stimulate the user's finger muscles to cause the user's hand to open, the arm muscles to relax, etc. (block 1212). Also, the pump activator 218 instructs the pump controller 124 to reverse the jamming of the jamming actuator(s) 108, 110, 112, 114. For example, the vacuum pump 120 sends air into the stiffened jamming actuator(s) 108, 110, 112, 114 via the vacuum pump hose(s) 126, 127, 129, 131, 133, 135 to cause the jamming actuator(s) 108, 110, 112, 114 to soften.

If the body movement detection sensor(s) 140 and/or the EMG sensor(s) 142 do not detect a change in limb position (block 1210), the analyzer 208 determines that the user 104 wishes to maintain the limb position. The jamming actuator(s) 108, 110, 112, 114 maintain their stiffened or rigid states until the analyzer 208 determines that the user 104 no longer wishes to hold the selected limb position.

Figure 13:
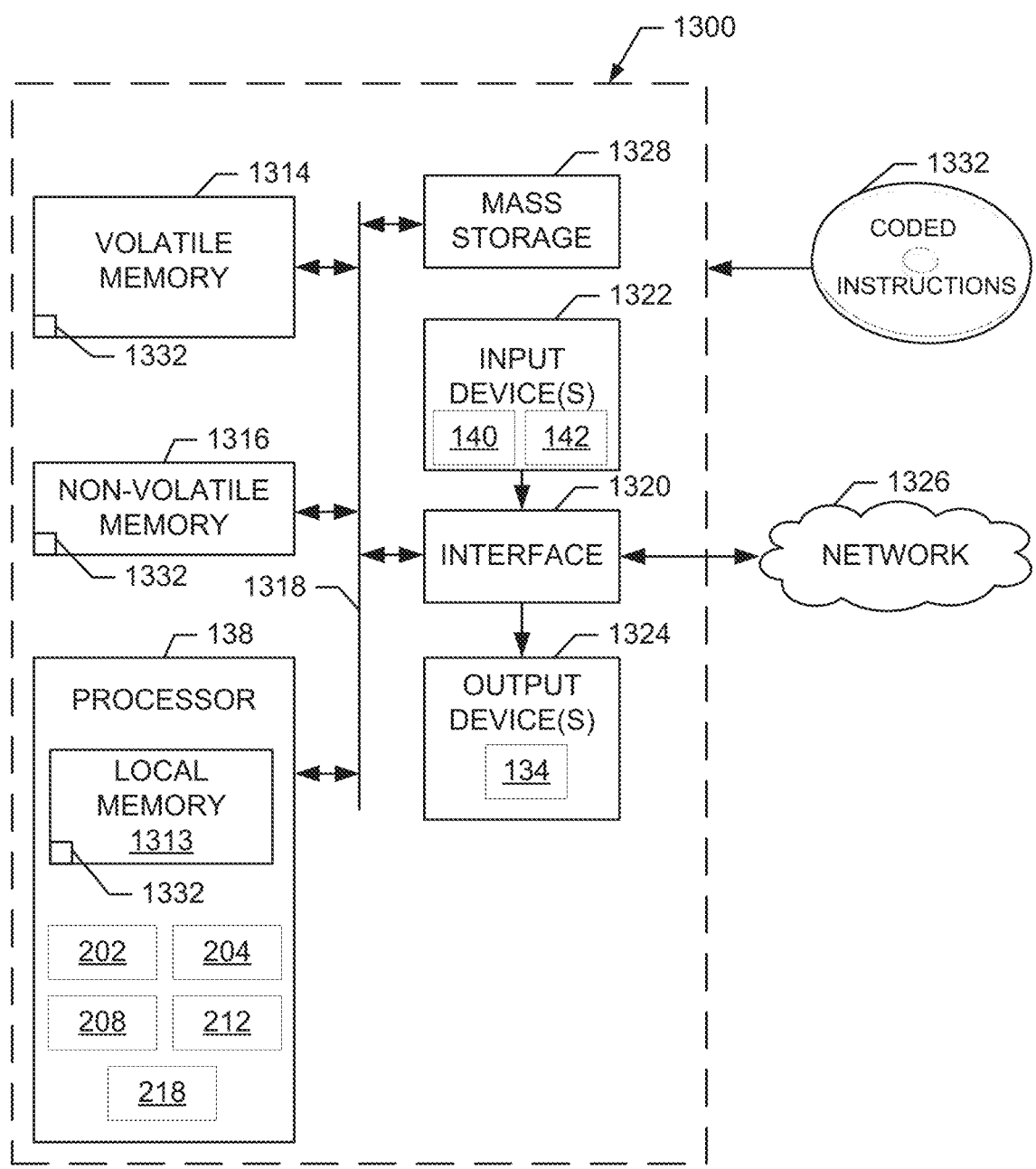
FIG. 13 illustrates an example processor platform that may execute the example instructions of FIG. 12 to implement the example system of FIGS. 1 and/or 2.

FIG. 13 is a block diagram of an example processor platform 1300 capable of executing the instructions of FIG. 12 to implement the example pump controller 124, the example EMS controller 138, the example EMS source 134, the example sensor data collector 202, the example database 204, the example analyzer 208, the example EMS activator 212, the example pump activator 218 and/or, more generally, the example system 100 of FIGS. 1A, 1B, and/or 2. The processor platform 1300 can be, for example, a server, a personal computer, a mobile device (e.g., a cell phone, a smart phone, a tablet such as an iPad™), a personal digital assistant (PDA), an Internet appliance, or any other type of computing device.

The processor platform 1300 of the illustrated example includes the processor 138. The processor 138 of the illustrated example is physical hardware implemented by a semiconductor-based device. For example, the processor 138 can be implemented by one or more integrated circuits, logic circuits, microprocessors or controllers from any desired family or manufacturer.

The processor 138 of the illustrated example includes a local memory 1313 (e.g., a cache). The processor 138 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a memory controller.

The processor platform 1300 of the illustrated example also includes an interface circuit 1320. The interface circuit 1320 may be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 138. The input device(s) can be implemented by, for example, an audio sensor, a microphone, a camera (still or video), a keyboard, a button, a mouse, a touchscreen, a track-pad, a trackball, isopoint, a voice recognition system, the body movement detection sensor(s) 140, and/or the EMG sensors 142.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1320 of the illustrated example, thus, typically includes a graphics driver card, a graphics driver chip or a graphics driver processor. In the example system 100 of FIGS. 1A, 1B, and/or 2, the output devices 1324 can include the electrodes 134.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

The coded instructions 1332 of FIG. 12 may be stored in the mass storage device 1328, in the volatile memory 1314, in the non-volatile memory 1316, and/or on a removable non-transitory computer readable storage medium such as a CD or DVD.

From the foregoing, it will be appreciated that methods, systems, and apparatus have been disclosed to provide a wearable assistive device that uses one or more jamming actuators to support a limb of the user in a desired position. Disclosed examples combine electrical stimulation of the muscles with use of the jamming actuators to assist the user in moving and/or supporting one or more of his or her body parts (e.g., arm, hand) as the user performs tasks such as grasping a cup. Disclosed examples selectively activate the electrical stimulation of the muscles and/or actuate the jamming actuators (e.g., based on voluntary movements) by the user, thereby allowing the user to substantially control limb movement and position. Disclosed examples provide for wearable assistive devices that are portable and comfortable to wear and that enable substantially smooth transitions between resting and active body part positions via on-demand control of the electrical stimulation of the muscles and/or the jamming actuators.

Example methods, apparatus, systems, and articles of manufacture to support one or more body parts of a user via a wearable assistive jamming device are disclosed herein. The following is a non-exclusive list of examples disclosed herein. Other examples may be included above. In addition, any of the examples disclosed herein can be considered in whole or in part, and/or modified in other ways.

Example 1 is an apparatus including a frame to be worn about a body part of a user, a jamming actuator carried by the frame, and an electrode to deliver electricity from an electrical source communicatively coupled to the electrode to a muscle of the user. The jamming actuator is to transition from a flexible state to a substantially rigid state in coordination with the delivery of the electricity to the electrode to support the body part.

Example 2 includes the apparatus as defined in example 1, further including a vacuum pump in fluid communication with the jamming actuator and a processor to control the vacuum pump to apply a vacuum to the jamming actuator in response to the delivery of the electricity to the electrode.

Example 3 includes the apparatus as defined in examples 1 or 2, further including a vacuum pump hose. The vacuum pump hose is to fluidly couple the vacuum pump to the jamming actuator.

Example 4 includes the apparatus as defined in examples 1 or 2, further including a sensor to detect a movement of the body part, the electrical source to provide the electricity in response to the detection of the movement of the body part.

Example 5 includes the apparatus as defined in example 4, wherein at least one of the transition of the jamming actuator from the flexible state to the substantially rigid state or a transition of the jamming actuator from the substantially rigid state to the flexible state, is in response to the movement of the body part.

Example 6 includes the apparatus as defined in example 5, wherein the movement is a first change in position of the body part from a first position to a second position. The sensor is to detect a second change in position of the body part from the second position to the first position. The transition of the jamming actuator from the substantially rigid state to the flexible state occurs in response to the detection of the second change in position.

Example 7 includes the apparatus as defined in example 4, wherein the sensor is one or more of an accelerometer or a pressure sensor.

Example 8 includes the apparatus as defined in example 1, wherein the jamming actuator includes a membrane and a ratchet disposed in the membrane.

Example 9 includes the apparatus as defined in example 1, wherein the jamming actuator includes a membrane, a first set of teeth disposed in the membrane and a second set of teeth disposed in the membrane. The first and second sets of teeth are to engage when the jamming actuator is in the substantially rigid state.

Example 10 includes the apparatus as defined in example 1, wherein the electrode is to detect electrical activity of the muscle prior to the delivery of the electricity. The electrical source is to provide the electricity in response to the detection of the electrical activity of the muscle.

Example 11 is a method including detecting, with a sensor worn by a user, a movement of a body part of the user; delivering, in response to the movement, an electrical current to the body part via an electrode; and actuating, in response to the movement, a jamming actuator to transition from a flexible state to a substantially rigid state.

Example 12 includes the method as defined in example 11, wherein the detecting of the movement of body part includes analyzing position data collected by the sensor relative to a position threshold.

Example 13 includes the method as defined in examples 11 or 12, wherein the detecting of the movement of the body part includes analyzing electrical activity data collected by the sensor relative to an amplitude threshold.

Example 14 includes the method as defined in example 11, further including actuating the jamming actuator in response to the delivering of the electrical current to the body part.

Example 15 includes the method as defined in any of examples 11, 12, or 14, wherein the actuating of the jamming actuator includes instructing a vacuum pump fluidly coupled to the jamming actuator to cause the vacuum pump to remove air from the jamming actuator.

Example 16 includes the method as defined in example 15, wherein the movement is a first movement and further including detecting a second movement of the body part; and instructing the processor of the vacuum pump to cause the vacuum pump to deliver fluid to the jamming actuator to transition from the substantially rigid state to the flexible state based on the detection of the second movement.

Example 17 includes the method as defined in example 16, further including delivering the electrical current to the body part based on the detection of the second movement of the body part.

Example 18 is a non-transitory computer readable medium comprising instructions that, when executed, cause a machine to at least detect a movement of a body part of the user based on data collected by a sensor worn by a user, deliver, in response to the movement, an electrical current to the body part, and actuate, in response to the movement, a jamming actuator to transition from a flexible state to a substantially rigid state.

Example 19 includes the non-transitory computer readable medium as defined in example 18, wherein the instructions, when executed, cause the machine to detect the movement of body part by analyzing the data collected by the sensor.

Example 20 includes the non-transitory computer readable medium as defined in examples 18 or 19, wherein the instructions, when executed, cause the machine to detect the movement of the body part by analyzing the data collected by the sensor relative to an amplitude threshold.

Example 21 includes the non-transitory computer readable medium as defined in example 18, wherein the instructions, when executed, cause the machine to actuate the jamming actuator in coordination with the delivering of the electrical current to the body part.

Example 22 includes the non-transitory computer readable medium as defined in any of examples 18, 19, or 21, wherein the instructions, when executed, cause the machine to actuate the jamming actuator by instructing a vacuum pump fluidly coupled to the jamming actuator to cause the vacuum pump to remove fluid from the jamming actuator.

Example 23 includes the non-transitory computer readable medium as defined in example 18, wherein the movement is a first movement and the instructions, when executed, cause the machine to detect a second movement of the body part, and instruct the vacuum pump to cause the vacuum pump to deliver fluid to the jamming actuator to transition from the substantially rigid state to the flexible state based on the detection of the second movement.

Example 24 includes the non-transitory computer readable medium as defined in example 23, wherein the instructions, when executed, cause the machine to deliver the electrical current to the body part based on the detection of the second movement of the body part.

Example 25 is an apparatus including a frame to be worn about a body part of a user and a jamming actuator carried by the frame. The jamming actuator includes a membrane, a first support disposed in the membrane, and a second support disposed in the membrane, the second support moveable relative to the first support when the jamming actuator is in a flexible state.

Example 26 includes the apparatus as defined in example 25, wherein the membrane includes an elastomeric material. A hardness of at least one of the first support or the second support is larger than a hardness of the elastomeric membrane.

Example 27 includes the apparatus as defined in example 25, wherein the second support is slidable relative to the first support when the body part moves from a first position to a second position.

Example 28 includes the apparatus as defined in examples 25 or 26, wherein the first support includes a plurality of teeth and a plurality of grooves formed between respective ones of the teeth. The second support is to engage one of the grooves when the jamming actuator is in a substantially rigid state.

Example 29 includes the apparatus as defined in example 25, wherein the first support and the second support are to enmesh when the jamming actuator is in a substantially rigid state.

Example 30 includes the apparatus as defined in examples 25 or 26, wherein the first support is a gear and the second support is a pawl.

Example 31 includes the apparatus as defined in examples 25 or 26, wherein the first support includes a rack having a plurality of teeth and the second support includes a ring, the ring to slide relative to the teeth.

Example 32 includes the apparatus as defined in example 25, wherein the first support includes a pocket defined in the membrane and the second support include a solid particle. The solid particle is to be disposed in the pocket.

Example 33 includes the apparatus as defined in example 32, wherein when the jamming actuator is in the flexible state, the solid particle is to rotate in the pocket.

Example 34 include the apparatus as defined in example 25, 25, wherein the membrane is a first membrane and the first support includes a second membrane at least partially overlapping the first membrane. A length of the second membrane is to expand when the body part moves to a bent position.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
   the frame structured to be worn about a body part of a user;
   a jamming actuator carried by the frame;
   an electrode structured to deliver electricity from an electrical source communicatively coupled to the electrode to a muscle of the user;
   a sensor structured to detect a first movement of the body part and to detect a second movement of the body part; and
   a processor in communication with the jamming actuator and the electrical source, the processor structured to:
      generate a first instruction to cause the jamming actuator to transition from a flexible state to a stiffened state in coordination with the delivery of the electricity to the electrode to support the body part in response to the first movement of the body part; and
      generate a second instruction to cause the jamming actuator to transition from the stiffened state to the flexible state in coordination with the delivery of the electricity to the electrode to release the body part in response to the second movement.

2. The apparatus of claim 1, further including:
   a vacuum pump in fluid communication with the jamming actuator,
   the processor structured to control the vacuum pump to apply a vacuum to the jamming actuator in response to the delivery of the electricity to the electrode.

3. The apparatus of claim 2, further including a vacuum pump hose structured to fluidly couple the vacuum pump to the jamming actuator.

4. The apparatus of claim 1 wherein the first movement is a first change in position of the body part from a first position to a second position and the second movement is a second change in position of the body part from the second position to the first position.

5. The apparatus of claim 1, wherein the jamming actuator includes a membrane, a first set of teeth disposed in the membrane and a second set of teeth disposed in the membrane, the first and second sets of teeth to engage when the jamming actuator is in the stiffened state.

6. The apparatus of claim 1, wherein the first instruction is to cause the jamming actuator to transition from the flexible state to the stiffened state in response to the delivery of the electricity to the electrode.

7. The apparatus of claim 1, wherein the first instruction is to cause the jamming actuator to transition from the flexible state to the stiffened state in advance of the delivery of the electricity to the electrode.

8. A method comprising:
   detecting, with a sensor worn by a user, a first movement of a body part of the user and a second movement of the body part of the user;
   delivering, in response to the first movement, a first electrical current to the body part via an electrode;
   actuating, by a processor and in response to the first movement and in coordination with the delivering of the first electrical current, a jamming actuator to transition from a flexible state to a stiffened state;
   delivering, in response to the second movement, a second electrical current to the body part via the electrode; and
   causing, in response to the second movement and in coordination with the delivering of the second electrical current, the jamming actuator to transition from the stiffened state to the flexible state.

9. The method of claim 8, wherein the detecting of the first movement of the body part includes analyzing, by the processor, position data collected by the sensor to determine a position of the body part relative to a threshold position.

10. The method of claim 8, wherein the detecting of the first movement of the body part includes analyzing, by the processor, electrical activity data collected by the sensor relative to an electrical signal amplitude threshold.

11. The method of claim 8, further including actuating the jamming actuator in response to the delivering of the first electrical current to the body part in response to the first movement.

12. The method of claim 8, wherein the actuating of the jamming actuator includes instructing, by the processor, a vacuum pump fluidly coupled to the jamming actuator to cause the vacuum pump to remove air from the jamming actuator.

13. The method of claim 12, further including causing, by a processor of the vacuum pump, the vacuum pump
   to deliver fluid to the jamming actuator to transition from the stiffened state to the flexible state in response to the second movement.

14. The method of claim 8, further including actuating the jamming actuator in advance of the delivering of the first electrical current to the body part in response to the first movement.

15. A non-transitory computer readable medium comprising instructions that, when executed, cause a machine to at least:
   detect a first movement of a body part of a user based on data collected by a sensor structured to be worn by the user and a second movement of the body part based on the data collected by the sensor;
   deliver, in response to the first movement, a first electrical current to the body part;
   actuate, in response to the first movement and in coordination with the delivery of the first electrical current, a jamming actuator to transition from a flexible state to a stiffened state;
   deliver, in response to the second movement, a second electrical current to the body part; and
   instruct, in response to the second movement and in coordination with the delivery of the second electrical current, the jamming actuator to transition from the stiffened state to the flexible state.

16. The non-transitory computer readable medium of claim 15, wherein the instructions, when executed, cause the machine to detect the first movement of the body part by analyzing the data collected by the sensor to determine a position of the body part relative to a threshold position.

17. The non-transitory computer readable medium of claim 15, wherein the instructions, when executed, cause the machine to detect the first movement of the body part by analyzing the data collected by the sensor relative to an electrical signal amplitude threshold.

18. The non-transitory computer readable medium of claim 15, wherein the instructions, when executed, cause the machine to actuate the jamming actuator in response to the delivery of the first electrical current to the body part in response to the first movement.

19. The non-transitory computer readable medium of claim 15, wherein the instructions, when executed, cause the machine to actuate the jamming actuator by instructing a vacuum pump fluidly coupled to the jamming actuator to remove fluid from the jamming actuator.

20. The non-transitory computer readable medium of claim 15, wherein the instructions, when executed, cause the machine to actuate the jamming actuator in advance of the delivery of the first electrical current to the body part in response to the first movement.

\* \* \* \* \*